United States Patent
Wada et al.

(10) Patent No.: US 9,669,386 B2
(45) Date of Patent: Jun. 6, 2017

(54) PARTICULATE WATER-ABSORBING AGENT AND PRODUCTION METHOD FOR THE SAME

(75) Inventors: Katsuyuki Wada, Himeji (JP); Yasuhisa Nakashima, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 217 days.

(21) Appl. No.: 13/876,728

(22) PCT Filed: Sep. 30, 2011

(86) PCT No.: PCT/JP2011/072619
§ 371 (c)(1),
(2), (4) Date: Mar. 28, 2013

(87) PCT Pub. No.: WO2012/043821
PCT Pub. Date: Apr. 5, 2012

(65) Prior Publication Data
US 2013/0175473 A1    Jul. 11, 2013

(30) Foreign Application Priority Data

Sep. 30, 2010 (JP) ................ 2010-222533
May 26, 2011 (JP) ................ 2011-118003

(51) Int. Cl.
| | |
|---|---|
| B01J 20/28 | (2006.01) |
| B01J 20/22 | (2006.01) |
| B01J 20/26 | (2006.01) |
| B01J 20/30 | (2006.01) |
| A61L 15/60 | (2006.01) |
| C08F 220/06 | (2006.01) |
| C08J 3/24 | (2006.01) |
| C08J 3/20 | (2006.01) |

(52) U.S. Cl.
CPC ......... *B01J 20/28011* (2013.01); *A61L 15/60* (2013.01); *B01J 20/223* (2013.01); *B01J 20/267* (2013.01); *B01J 20/3085* (2013.01); *C08F 220/06* (2013.01); *C08J 3/203* (2013.01); *C08J 3/245* (2013.01); *C08J 2333/02* (2013.01)

(58) Field of Classification Search
CPC ...... C08L 33/02; C08F 220/10; C08F 220/06; B01J 20/28011; B01J 20/223; B01J 20/267; B01J 20/3085; A61L 15/60; C08J 3/245; C08J 3/203; C08J 2333/02
USPC ............. 524/556, 557, 503, 437; 526/317.1
See application file for complete search history.

(56) References Cited

U.S. PATENT DOCUMENTS

| | | | |
|---|---|---|---|
| 5,562,646 A | 10/1996 | Goldman et al. | |
| 6,156,678 A | 12/2000 | Mukaida et al. | |
| 6,300,275 B1 | 10/2001 | Weir | |
| 6,414,214 B1 | 7/2002 | Engelhardt et al. | |
| 6,849,665 B2 | 2/2005 | Frenz et al. | |
| 7,169,843 B2 | 1/2007 | Smith et al. | |
| 7,173,086 B2 | 2/2007 | Smith et al. | |
| 7,282,262 B2 | 10/2007 | Adachi et al. | |
| 7,473,470 B2 | 1/2009 | Ishizaki et al. | |
| 7,745,537 B2 * | 6/2010 | Nakashima | A61L 15/60 252/194 |
| 7,825,169 B2 | 11/2010 | Wada et al. | |
| 8,198,209 B2 * | 6/2012 | Torii | A61L 15/18 428/326 |
| 8,596,931 B2 | 12/2013 | Nagashima et al. | |
| 8,952,116 B2 | 2/2015 | Kobayashi et al. | |
| 2003/0069359 A1 | 4/2003 | Torii et al. | |
| 2004/0048955 A1 | 3/2004 | Wada et al. | |
| 2005/0118423 A1 * | 6/2005 | Adachi | A61L 15/60 428/402 |
| 2005/0256469 A1 | 11/2005 | Qin et al. | |
| 2008/0125533 A1 | 5/2008 | Riegel et al. | |
| 2009/0202805 A1 | 8/2009 | Furno et al. | |
| 2010/0119312 A1 * | 5/2010 | Nagashima | A61L 15/60 406/46 |
| 2010/0323885 A1 | 12/2010 | Herfert et al. | |
| 2011/0003926 A1 | 1/2011 | Nogi et al. | |
| 2012/0184670 A1 | 7/2012 | Kobayashi et al. | |

FOREIGN PATENT DOCUMENTS

| | | | |
|---|---|---|---|
| CN | 1578820 | 2/2005 | |
| CN | 1697859 | 11/2005 | |
| CN | 102548654 | 4/2012 | |
| EP | 1191051 A2 * | 3/2002 | |
| JP | 11-128355 | 2/1999 | |
| JP | EP 1191051 A2 * | 3/2002 | ............ A61L 15/60 |
| JP | 2004-261796 | 9/2004 | |
| JP | 2005-105254 | 4/2005 | |
| JP | 2005-113117 | 4/2005 | |
| JP | 2005-344103 | 12/2005 | |
| JP | 2006-57075 | 3/2006 | |
| JP | WO 2007116777 A1 * | 10/2007 | ............ A61L 15/18 |
| JP | 2009227885 A | 10/2009 | |
| WO | WO-03/090801 A1 | 11/2003 | |
| WO | WO 2007116777 A1 * | 10/2007 | |
| WO | WO2008/120742 | 10/2008 | |
| WO | WO 2011/040472 A1 | 4/2011 | |

OTHER PUBLICATIONS

Buccholz et al., "Modern Superabsorbent Polymer Technology," (1998) 149-147.

* cited by examiner

*Primary Examiner* — Michael M Bernshteyn
(74) *Attorney, Agent, or Firm* — Cesari and McKenna, LLP

(57) ABSTRACT

A particulate water-absorbing agent containing a surface-crosslinked polyacrylic acid (salt)-type water-absorbing resin as a main component and at least one spacer selected from a polycation and water-insoluble fine particles. The particulate water-absorbing agent has a free swell capacity (FSC) of 55 to 65 g/g, an absorption against pressure (AAP—4.83 kPa) of 20 to 30 g/g, and a vertical diffusion absorption amount under pressure (VDAUP—4.83 kPa) of 30 to 80 g. Also disclosed is a method for producing a particulate water-absorbing agent, an absorbent core containing the particulate water-absorbing agent, and an absorbing article containing the absorbent core.

25 Claims, 1 Drawing Sheet

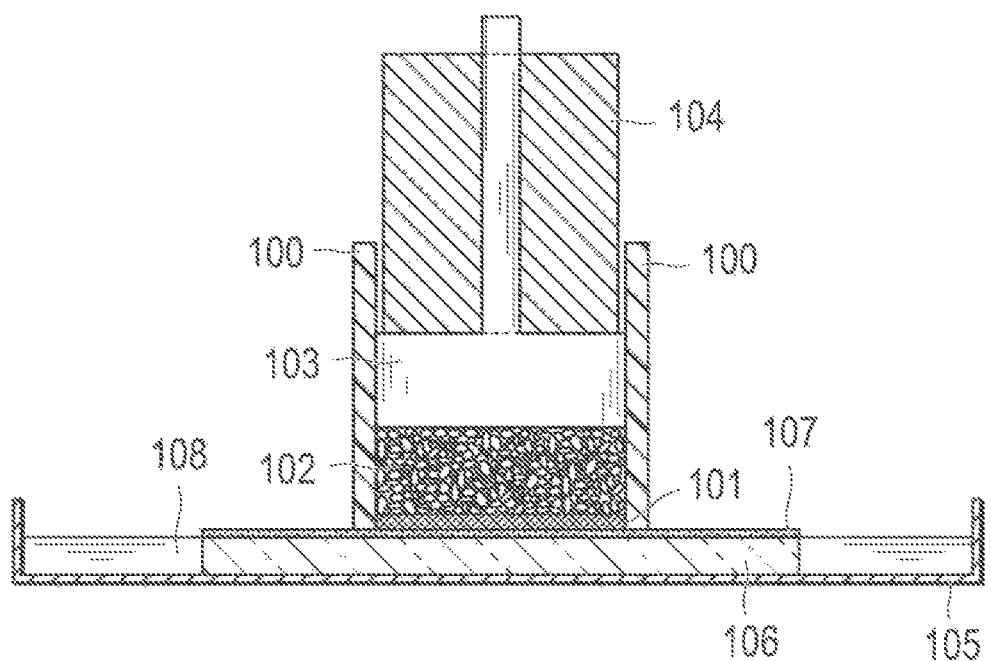

PARTICULATE WATER-ABSORBING AGENT AND PRODUCTION METHOD FOR THE SAME

CROSS REFERENCE TO RELATED APPLICATIONS

This application is a National Stage of International Application No. PCT/JP2011/072619 filed on Sep. 30, 2011, which claims priority to Japanese Application No. 2010-222533 filed Sep. 20, 2010 and Japanese Application No. 2011-118003 filed May 26, 2011, the contents of which are hereby incorporated by reference in their entirety.

TECHNICAL FIELD

The present invention relates to a particulate water-absorbing agent and a method for producing the same. More particularly, the present invention relates to a particulate water-absorbing agent containing a polyacrylic acid (salt)-type water-absorbing resin as a main component, the particulate water-absorbing agent having particular water absorption performance, and a method for producing the same.

BACKGROUND ART

Currently, in the applications as the constituent materials for absorbing articles such as paper diapers, sanitary napkins and incontinence pads, water-absorbing agents containing water-absorbing resins as a main component are widely used, in addition to hydrophilic fibers such as pulp.

Known examples of water absorption characteristics that are desired in the water-absorbing resins include centrifuge retention capacity, absorption against pressure, liquid permeability, rate of water absorption, water-extractable, and gel strength, and many suggestions have been made so far on the methods for measuring or enhancing these physical properties (methods for producing water-absorbing resins), as well as patents for parameters that define these physical properties (water-absorbing resins or water-absorbing agents).

Among the physical properties described above, the centrifuge retention capacity is the most fundamental property, and the methods for measuring the property are roughly classified into methods in which a water-absorbing resin is caused to swell in physiological saline and then dehydration is carried out by centrifugation (CRC method: Centrifuge Retention Capacity method; centrifugation method), and methods in which dehydration is carried out by suspending the water-absorbing resin, without performing centrifugation (FSC method: Free Swell Capacity method; also known as TB method). The absorption capacities obtained by these measurement methods are generally known to correlate with each other (for example, FSC=1.02×CRC+11.32; Non-Patent Literature 1, page 152). However, since the absorption capacity according to the CRC method expresses the absorption capacity of a water-absorbing resin itself while sufficiently excluding the interstitial water at the time of swelling, evaluations according to the CRC method are generally used for the present, and the CRC method is employed in many Patent Literatures and in the step management for water-absorbing resins.

Furthermore, examples of the basic physical properties of a water-absorbing resin other than the centrifuge retention capacity (CRC) include the absorption against pressure (AAP) and liquid permeability (for example, SFC and GBP), and many suggestions have been made on a water-absorbing resin which has these physical properties controlled, or methods for controlling the physical properties.

For example, Patent Literature 1 discloses a method for producing a high liquid-permeable water-absorbing agent, in which when a water-absorbing agent is produced by mixing water-absorbing resin particles with a metal compound (a metal salt, a metal cation, or the like), the metal component is prevented from penetrating into the interior of the water-absorbing resin particles, and also the metal component uniformly adheres in the form of fine dots to the overall surface of the water-absorbing resin.

Patent Literature 2 discloses a method for producing a water-absorbing agent having the gel blocking properties, liquid permeability and liquid diffusibility improved all at the same time.

Patent Literature 3 discloses, as a method for producing a water-absorbing agent which exhibits high gel bed permeability (GBP), does not have a tendency of aggregation or caking, and does not have a tendency to form dust, a method for producing a superabsorbent which is re-wetted and surface-crosslinked, the method including a step for bringing a superabsorbent base polymer, an organic crosslinking agent and a polyvalent metal salt solution into contact in the presence of an alcohol, subjecting the mixture to a heat treatment to produce a dry superabsorbent that has been surface-crosslinked, and re-wetting the surface-crosslinked dry superabsorbent.

Patent Literature 4 discloses a method for producing a water-absorbing polymer structure having high absorption capacity, the method including steps of preparing an untreated water-absorbing polymer structure (Pu) having a particular retentivity; and bringing the untreated water-absorbing polymer structure (Pu) into contact with a permeability enhancing agent which is preferably a SiO compound, a salt containing a polyvalent (preferably trivalent) cation, or a mixture of a SiO compound and a salt containing a polyvalent (preferably trivalent) cation, in order to provide a water-absorbing polymer structure which is capable of enhancing the absorption and dispersion of a liquid when used in an absorptive structures such as, for example, a disposable diaper, as compared with conventional absorbing agents.

Patent Literature 5 discloses a method of obtaining a highly absorptive polymer having excellent liquid permeability, by mixing a polyvalent metal salt and a highly absorptive polymer by dry blending.

Furthermore, as methods for evaluating liquid permeability, many methods or technologies for improving liquid permeability under load or liquid permeability under no load, such as a SFC method (Saline Flow conductivity; Patent Literature 6) and a GBP method (Gel Bed Permeability; Patent Literatures 7 to 9). Furthermore, in regard to such physical properties, many combinations of plural parameters including liquid permeability have also been suggested, and there are known a technology for defining impact resistance (FI) (Patent Literature 10), a technology for defining the rate of water absorption (FSR and/or Vortex) (Patent Literature 11), and a technology for defining the product of liquid diffusion performance (SFC) and the core absorption amount after 60 minutes (DA60) (Patent Literature 12).

CITATION LIST

Patent Literature

Patent Literature 1: JP 2005-344103 A
Patent Literature 2: JP 2005-113117 A

Patent Literature 3: US 2010/0323885
Patent Literature 4: US 2009/0202805
Patent Literature 5: U.S. Pat. No. 6,300,275
Patent Literature 6: U.S. Pat. No. 5,562,646
Patent Literature 7: US 2005/0256469
Patent Literature 8: U.S. Pat. No. 7,169,843
Patent Literature 9: U.S. Pat. No. 7,173,086
Patent Literature 10: U.S. Pat. No. 6,414,214
Patent Literature 11: U.S. Pat. No. 6,849,665
Patent Literature 12: US 2008/125533

Non-Patent Literature

Non-Patent Literature 1: Modern Superabsorbent Polymer Technology (1998) p. 149-157, FIG. 4.21

SUMMARY OF INVENTION

Technical Problem

However, if only the basic physical properties described above are controlled, when a water-absorbing agent is used in a disposable diaper, the diffusibility into the disposable diaper or the rate of water absorption are improved to a certain extent, but it has been the situation that the improvement of the absolute absorption amount or the re-wet amount cannot be said to be sufficient.

For example, it is known that liquid permeability and the centrifuge retention capacity are contradictory to each other, and as described above, numerous water-absorbing resins having improved liquid permeation performance have been suggested in Patent Literatures 1 to 5 and the like. Particularly, in order to enhance the liquid permeation performance, attempts have been made to increase the gel strength or to impart liquid permeation performance to a water-absorbing resin by means of additives. However, all of the suggestions and attempts are focused on the performance of water-absorbing resins that puts more weight to liquid permeability or diffusibility, results satisfactory from the viewpoints of the liquid absorption time, the re-wet amount, the absorption amount in a disposable diaper of actual use cannot be obtained, and particularly, the absorption amount (also known as: absolute absorption amount) of paper diapers has not been satisfactory.

Furthermore, in regard to the method for producing a water-absorbing resin, attempts have been made to use a water-absorbing resin having a low centrifuge retention capacity, or to subject a water-absorbing resin to an excessive surface-crosslinking treatment, and to thereby lower the centrifuge retention capacity as a result, in order to enhance the absorption against pressure or the liquid permeation performance. However, this measure implies that high absorption against pressure (AAP) or high liquid permeability (SFC or GBP) is obtained by sacrificing the centrifuge retention capacity (CRC). Thus, there has been a problem that in order to use the water-absorbing agent (or water-absorbing resin) thus obtained in an absorbent core and to increase the absorption amount as the absorbent core, the using amount of the water-absorbing agent inevitably increases.

That is, the present invention was made in view of such problems, and it is an object of the present invention to provide a water-absorbing agent which can provide an absorbent core having a large absorption amount in a disposable diaper, having improved liquid diffusibility and liquid permeability, and having a smaller re-wet amount, at a low price.

Furthermore, another object of the present invention is to provide a water-absorbing agent having an improved liquid absorption time, an improved re-wet amount, or an improved absolute absorption amount in a disposable diaper, in relation to water-absorbing resins that have been conventionally evaluated on the centrifuge retention capacity (CRC) as well as the absorption against pressure (for example, AAP) or liquid permeability (for example, SFC or GBP), and a method for producing the water-absorbing agent.

Solution to Problem

In order to solve the problems described above, the inventors of the present invention conducted a thorough investigation, and as a result, the inventors found that with regard to water-absorbing resins that have been traditionally defined by many parameters, a novel parameter called vertical diffusion absorption amount under pressure (VDAUP) greatly affects the re-wet amount of a disposable diaper. Furthermore, the inventors found that while CRC and FSC in the absorption capacities under no added pressure are correlated with each other (Non-Patent Literature 1), when a small amount of a particular spacer is added to a water-absorbing resin having an centrifuge retention capacity (CRC) and an absorption against pressure (AAP) in particular ranges, the suspension factor (FSC) is greatly improved as compared with the centrifuge retention capacity (CRC). The inventors also found a novel water-absorbing agent which maintains the vertical diffusion absorption amount under pressure (VDAUP), FSC and AAP in certain high ranges, and has an improved re-wet amount in a disposable diaper and an improved absolute absorption amount, is obtained by controlling the FSC to a particular narrow range, and thus the inventors completed the present invention.

More specifically, a particulate water-absorbing agent according to the present invention contains a surface-crosslinked polyacrylic acid (salt)-type water-absorbing resin as a main component, and contains at least one spacer selected from a polycation and water-insoluble fine particles. The particulate water-absorbing agent satisfies an free swell capacity (FSC) of 55 to 65 [g/g], an absorption against pressure (AAP—4.83 kPa) of 20 to 30 [g/g], and a vertical diffusion absorption amount under pressure (VDAUP—4.83 kPa) of 30 to 80 g.

Furthermore, a first method for producing a particulate water-absorbing agent according to the present invention is a method for producing a particulate water-absorbing agent containing a polyacrylic acid (salt)-type water-absorbing resin as a main component, the method including a polymerization step for a water-soluble unsaturated monomer containing acrylic acid (salt) as a main component, a drying step, and a surface-crosslinking step, the method including the following steps (A), (B) and (C):

Step (A): a step for obtaining water-absorbing resin particles having an centrifuge retention capacity (CRC) of 40 to 56 [g/g] before the surface-crosslinking step;

Step (B): a step for surface-crosslinking the water-absorbing resin particles obtained in the step (A), and thereby obtaining a water-absorbing resin powder having an centrifuge retention capacity (CRC) of 32 to 40 [g/g] and an absorption against pressure (AAP—4.83 kPa) of 20 to 30 [g/g]; and Step (C): a step for mixing the water-absorbing resin powder obtained in the step (B) with a spacer, and thereby adjusting the decrement of the absorption against pressure (AAP—4.83 kPa) to 5 [g/g] or less.

Furthermore, a second method for producing a particulate water-absorbing agent according to the present invention is a method for producing a particulate water-absorbing agent containing a polyacrylic acid (salt)-type water-absorbing resin as a main component, the method including a polymerization step for polymerizing a water-soluble unsaturated monomer containing acrylic acid (salt) as a main component, a drying step, and a surface-crosslinking step, the method including the following steps (A), (B) and (D):

Step (A): a step for obtaining water-absorbing resin particles having an centrifuge retention capacity (CRC) of 40 to 56 [g/g] before the surface-crosslinking step;

Step (B): a step for surface-crosslinking the water-absorbing resin particles obtained in the step (A), and thereby obtaining a water-absorbing resin powder having an centrifuge retention capacity (CRC) of 32 to 40 [g/g] and an absorption against pressure (AAP—4.83 kPa) of 20 to 30 [g/g]; and Step (D): a step for mixing 100 parts by weight of the water-absorbing resin powder obtained in the step (B) with 0.001 parts to 3 parts by weight of a polyvalent metal cation as an aqueous solution.

Furthermore, a third method for producing a particulate water-absorbing agent according to the present invention is a method for producing a particulate water-absorbing agent containing a polyacrylic acid (salt)-type water-absorbing resin as a main component, the method including a polymerization step for polymerizing a water-soluble unsaturated monomer containing acrylic acid (salt) as a main component, a drying step, and a surface-crosslinking step, the method including the following steps (A), (B) and (E):

Step (A): a step for obtaining water-absorbing resin particles having an centrifuge retention capacity (CRC) of 40 to 56 [g/g] before the surface-crosslinking step;

Step (B): a step for surface-crosslinking the water-absorbing resin particles obtained in the step (A), and thereby obtaining a water-absorbing resin powder having an centrifuge retention capacity (CRC) of 32 to 40 [g/g] and an absorption against pressure (AAP—4.83 kPa) of 20 to 30 [g/g]; and Step (E): a step for mixing 100 parts by weight of the water-absorbing resin powder obtained in the step (B) with a polyamine polymer in an amount of greater than or equal to 0.001 parts by weight and less than 0.3 parts by weight as an aqueous solution or a powder.

Moreover, a fourth method for producing a particulate water-absorbing agent according to the present invention is a method for producing a particulate water-absorbing agent containing a polyacrylic acid (salt)-type water-absorbing resin as a main component, the method including a polymerization step for polymerizing a water-soluble unsaturated monomer containing acrylic acid (salt) as a main component, a drying step, and a surface-crosslinking step, the method including the following steps (A), (B) and (F):

Step (A): a step for obtaining water-absorbing resin particles having an centrifuge retention capacity (CRC) of 40 to 56 [g/g] before the surface-crosslinking step;

Step (B): a step for surface-crosslinking the water-absorbing resin particles obtained in the step (A), and thereby obtaining a water-absorbing resin powder having an centrifuge retention capacity (CRC) of 32 to 40 [g/g] and an absorption against pressure (AAP—4.83 kPa) of 20 to 30 [g/g]; and Step (F): a step for mixing 100 parts by weight of the water-absorbing resin powder obtained in the step (B) with 0.001 parts to 0.4 parts by weight of water-insoluble fine particles as a powder.

In addition, an absorbent core according to the present invention contains the particulate water-absorbing agent according to the present invention.

Advantageous Effects of Invention

When the particulate water-absorbing agent of the present invention is used, the particulate water-absorbing agent can be produced at low cost, and when the particulate water-absorbing agent is used in an absorbent core such as a disposable diaper, the absorption amount, the re-wet amount (Re-wet) and the liquid absorption time in the absorbent core are improved and are well-balanced to a better extent. Furthermore, when the particulate water-absorbing agent is produced as an absorbing article (particularly a disposable diaper), since the absorption amount of the disposable diaper can be made high, an effect of reducing the using amount of the water-absorbing resin (particulate water-absorbing agent) in one sheet of paper diaper is obtained, and even in an environmental viewpoint, the amount of disposal of the disposable diaper or the water-absorbing resin is also reduced.

BRIEF DESCRIPTION OF DRAWINGS

FIG. 1 is a schematic diagram illustrating an apparatus for measuring the AAP (absorption against pressure) or the vertical diffusion absorption amount under pressure (VDAUP) related to Examples of the present invention.

DESCRIPTION OF EMBODIMENTS

Hereinafter, the particulate water-absorbing agent related to the present invention and a method for producing the same will be described in detail, but the scope of the present invention is not intended to be restricted by these descriptions, and in addition to the following embodiments, appropriate modifications can be made to the extent that the purport of the present invention is not impaired. Specifically, the present invention is not intended to be limited to the various exemplary embodiments to be described below, and various modifications can be made within the scope defined in the claims. Exemplary embodiments obtainable by appropriately combining the technical means respectively disclosed in different exemplary embodiments are also included in the technical scope of the present invention.

[1] Definition of Terms (1-1) "Water-Absorbing Agent"

The "water-absorbing agent" according to the present invention means an absorbing and gelling agent (also known as: solidifying agent) for aqueous liquids, which contains a water-absorbing resin as a main component, and such an agent in a particulate form is particularly called a particulate water-absorbing agent. The relevant water-absorbing agent is not particularly limited as to whether the aqueous liquid is water alone or a water mixture, as long as the aqueous liquid contains water in the form of solid, liquid or gas, but the water-absorbing agent is used for the absorption of urine, particularly human urine.

Furthermore, the water-absorbing agent of the present invention may also contain other compounds, but from the viewpoint of water absorption characteristics, it is preferable that the water-absorbing agent contain a water-absorbing resin in an amount of preferably 60% by weight or greater, more preferably 70% by weight or greater, still more preferably 80% by weight or greater, and particularly preferably from 85% by weight to 99% by weight, and further contain a chelating agent, inorganic fine particles, water and the like as will be described below.

(1-2) "Water-Absorbing Resin"

The "water-absorbing resin" according to the present invention means a water-swellable, water-insoluble polymer gelling agent. Meanwhile, the term "water-swellable" means that the CRC (centrifuge retention capacity) as defined in ERT441.2-02 is 5 [g/g] or greater, and the term "water-insoluble" means that the Ext (water-extractable) as defined in ERT470.2-02 is 0% to 50% by weight.

The water-absorbing resin can be appropriately designed in accordance with the use, and is not particularly limited; however, the water-absorbing resin is preferably a hydrophilic crosslinked polymer obtained by crosslinking polymerizing an unsaturated monomer containing a carboxyl group. Furthermore, the water-absorbing resin is not limited to the case where the entire amount (100% by weight) is composed of a polymer, and the water-absorbing resin may be a water-absorbing resin composition containing additives and the like to the extent that the performance described above is maintained. Also, regardless of the presence or absence of surface crosslinking, there are no particular limitations on the shape of the water-absorbing resin, and the water-absorbing resin may be in a sheet form, a fiber form, a powder form, a film form, a gel form or the like, all of which are collectively called water-absorbing resins. Furthermore, in the present invention, in order to discriminate the water-absorbing resins obtainable before and after surface crosslinking, the water-absorbing resin obtained before surface crosslinking is referred to as "water-absorbing resin particles" and the water-absorbing resin obtained after surface crosslinking is referred to as "water-absorbing resin powder".

(1-3) "Polyacrylic Acid (Salt)"

The "polyacrylic acid (salt)" according to the present invention means a polymer which optionally contains a graft component and contains, as a main component, acrylic acid and/or a salt thereof (hereinafter, referred to as "acrylic acid (salt)") as a repeating unit. Specifically, the polyacrylic acid (salt) refers to a polymer which contains acrylic acid (salt) preferably in an amount of 30% to 100% by mole as a monomer excluding a crosslinking agent.

(1-4) "EDANA" and "ERT"

The "EDANA" is the abbreviation for the European Disposables and Nonwovens Association, and the term "ERT" is the abbreviation for a method for analyzing a water-absorbing resin (EDANA Recommended Test Method), which is a European standard (apparently international standard). In the present invention, unless particularly stated otherwise, the analysis is carried out according to the original document of ERT (published document: revised in 2002). Furthermore, the particulate water-absorbing agent of the present invention can also be analyzed according to the original document of ERT in the same manner.

(a) [CRC] (ERT441.2-02)

The term "CRC" is the abbreviation for Centrifuge Retention Capacity, and means the centrifuge retention capacity (hereinafter, may also be referred to as "absorption capacity". Furthermore, the term has the same meaning as "absorption capacity") of a water-absorbing resin. Specifically, the CRC is an absorption capacity (unit: [g/g]) obtained after 0.200 g of a water-absorbing resin in a non-woven fabric bag is immersed (allowed to freely swell) for 30 minutes in a large excess of a 0.9% by weight of aqueous solution of sodium chloride, and then is dehydrated in a centrifuge.

(b) "FSC" (ERT442.2-02)

The term "FSC" is the abbreviation for Free Swell Capacity, and means an absorption capacity under suspension without load of a water-absorbing resin. Specifically, the FSC is an absorption capacity (unit: [g/g]) obtained after 0.200 g of a water-absorbing resin in a non-woven fabric bag is immersed (allowed to freely swell) for 30 minutes in a large excess of a 0.9% by weight of aqueous solution of sodium chloride, and then is dehydrated by suspending for 10 minutes. Unlike the CRC, the amount of liquid retained in between the particles (interstices) of the water-absorbing resin can be evaluated.

(c) "AAP" (ERT442.2-02)

The term "AAP" is the abbreviation for Absorption capacity against Pressure, and means the absorption against pressure of a water-absorbing resin. Specifically, the AAP is the water absorption capacity (unit: [g/g]) obtained after 0.900 g of a water-absorbing resin in a non-woven fabric bag is allowed to swell for one hour in a large excess of a 0.9% by weight of aqueous solution of sodium chloride under a load of 2.06 kPa (0.3 psi, 21 [g/cm]). Meanwhile, in ERT442.2-02, the term is indicated as Absorption under Pressure, but this has substantially the same definition as AAP. Furthermore, the AAP may also be measured by changing the load conditions to 4.83 kPa (0.7 psi, 50 [g/cm$^2$]).

(d) "Ext" (ERT470.2-02)

The "Ext" is the abbreviation for Extractable, and means the water-extractable (amount of water-solubilized components) of a water-absorbing resin. Specifically, the Ext is the amount of dissolved polymer (unit: % by weight) obtained after 1.000 g of a water-absorbing resin is added to 200 ml of a 0.9% by weight of aqueous solution of sodium chloride, and is stirred for 16 hours at 500 rpm. The measurement of the amount of dissolved polymer is carried out by pH titration.

(e) "PSD" (ERT420.2-02)

The term "PSD" is the abbreviation for Particle Size Distribution, and means the particle size distribution of a water-absorbing resin measured by sieve classification. Furthermore, the mass median particle size (D50) and the particle size distribution width of a water-absorbing resin are measured by the same method as the method of "(1) Average Particle Diameter and Distribution of Particle Diameter" described in EP 0349240, page 7, lines 25-43.

(f) "pH" (ERT400.2-02)

The term "pH" means the pH of a water-absorbing resin, and is defined as the pH of a dispersion liquid containing a swollen gel obtained by dispersing a water-absorbing resin in a 0.9% by weight of aqueous solution of sodium chloride.

(1-5) "VDAUP"

The "VDAUP" according to the present invention is the abbreviation for Vertical Diffusion Absorption capacity under Pressure, and means the amount of vertical diffusion absorption under pressure of a water-absorbing resin. The VDAUP is a parameter based on a novel concept, and it has been found that the VDAUP is highly correlated with the re-wet amount or the absolute absorption amount in a disposable diaper. Specifically, the VDAUP refers to the amount of absorbed liquid (unit: [g]) obtained after 10.000 g of a water-absorbing resin is allowed to swell in a large excess of 0.9% by weight of aqueous solution of sodium chloride for one hour under a load of 4.83 kPa (0.7 psi, 50 [g/cm]). That is, the VDAUP differs from the absorption against pressure (AAP) only in the amount of sample and the load conditions used in the measurement, but the AAP is defined by weight ratio ([g/g]), while the VDAUP is defined by the absolute liquid amount ([g]).

Furthermore, since the VDAUP allows measurement at a basis weight of 11 times or more the basis weight of the AAP per unit area, in order to achieve uniform absorption of an aqueous liquid into the entirety of a sample, the liquid diffusibility and liquid permeability between swollen gel layers exert large influence. Therefore, the VDAUP not only indicates the absorption amount under pressure, but also serves as an index representing liquid diffusibility and liquid permeability in an actual absorber, particularly an absorbent core in which the proportion of use (concentration) of a water-absorbing resin is high. Meanwhile, Examples described below will disclose the fact that the VDAUP is highly correlated with the physical properties in a disposable diaper.

(1-6) Others

According to the present specification, the expression "X to Y" that indicates a range means "more than or equal to X and less than or equal to Y" including X and Y. Furthermore, the unit of weight, "t (ton)", means "metric ton", and "weight" and "mass", "% by weight" and "% by mass", and "parts by weight" and "parts by mass" are regarded as synonyms. Unless particularly stated otherwise, the unit "ppm" means "ppm by weight" or "ppm by mass". Furthermore, the term "-acid (salt)" means "-acid and/or a salt thereof", and "(meth)acryl" means "acryl and/or methacryl".

[2] Method for Producing Particulate Water-Absorbing Agent (2-1) Polymerization Step
(Monomer)

The water-absorbing resin (hereinafter, the water-absorbing resin before being surface-crosslinking treated may be particularly referred to as "water-absorbing resin particles") as a main component used in the particulate water-absorbing agent obtainable by the production method of the present invention, is a polyacrylic acid (salt)-type water-absorbing resin, and is a water-swellable, water-insoluble crosslinked polymer containing acrylic acid (salt) as a monomer in the repeating unit (provided that the crosslinking agent that will be described below is excluded) in an amount of preferably 30% to 100% by mole, more preferably 50% to 100% by mole, still more preferably 70% to 100% by mole, particularly preferably 90% to 100% by mole, and substantially 100% by mole.

It is preferable that the acid groups of the monomer be neutralized, and as a neutralized salt, a monovalent salt is preferred, more preferably an alkali metal salt or an ammonium salt, still more preferably an alkali metal salt, and particularly preferably a sodium salt in which 0% to 100% by mole, preferably 20% to 100% by mole, more preferably 50% to 99% by mole, and still more preferably 60% to 90% by mole, of the acid groups are neutralized.

(Other Monomer and Crosslinking Agent)

In the present invention, when a particulate water-absorbing agent is obtained, an unsaturated monomer other than acrylic acid (salt) (hereinafter, referred to as "other monomer") can be used in an amount of 0% to 70% by mole of the total amount of monomer components. Specific examples of the other monomer include hydrophilic unsaturated monomers such as methacrylic acid, maleic acid (anhydride), fumaric acid, crotonic acid, itaconic acid, vinyl-sulfonic acid, 2-(meth)acrylamido-2-methylpropanesulfonic acid, (meth)acryloxyalkanesulfonic acid, N-vinyl-2-pyrrolidone, N-vinylacetamide, (meth)acrylamide, N-isopropyl (meth)acrylamide, N,N-dimethyl (meth)acrylamide, 2-hydroxyethyl (meth)acrylate, methoxypolyethylene glycol (meth)acrylate, and polyethylene glycol (meth)acrylate; and salts thereof.

Furthermore, the crosslinking agent that can be used in the present invention is not particularly limited, but examples thereof include compounds capable of forming covalent bonds by reacting with carboxyl groups, for example, compounds having at least two polymerizable double bonds in the molecule, such as N,N'-methylenebisacrylamide, (poly) ethylene glycol di(meth)acrylate, (poly) propylene glycol di(meth)acrylate, (polyoxyethylene)trimethylolpropane tri (meth)acrylate, trimethylolpropane di(meth)acrylate, polyethylene glycol di(β-acryloyloxypropionate), trimethylolpropane tri(β-acryloyloxypropionate), and poly(meth) aryloxyalkane; and polyglycidyl ethers such as ethylene glycol diglycidyl ether; polyols such as ethylene glycol, polyethylene glycol, glycerin, and sorbitol. The crosslinking agent can be used singly, or two or more kinds can be used in combination. Meanwhile, in the case of using a crosslinking agent, it is preferable to use a compound having at least two polymerizable double bonds in the molecule, while considering the water absorption characteristics and the like of the particulate water-absorbing agent thus obtainable. The using amount of the crosslinking agent is preferably 0% to 5% by mole, and more preferably 0.001% to 2% by mole, with respect to the monomers from the viewpoint of physical properties. Furthermore, the using amount is still more preferably 0.01% to 0.1% by mole, particularly preferably 0.02% to 0.06% by mole, and most preferably 0.022% to 0.058% by mole.

Furthermore, in the present invention, a foaming agent, a deodorizing agent, an antibacterial agent, a plasticizer, a fragrance, a pigment, a dye, a hydrophilic short fiber, an inorganic powder of silicon oxide, titanium oxide or the like, a polysaccharide such as starch or cellulose or a derivative thereof, a hydrophilic polymer such as polyvinyl alcohol, a thermoplastic resin such as polyethylene or polypropylene, a chain transfer agent such as hypophosphorous acid (salt), and the like can be incorporated as necessary into the monomer described above, in an amount of preferably 5% by weight or less, and more preferably 1% by weight or less.

Furthermore, a water-absorbing resin or a water-soluble resin may also be incorporated into the monomer at the time of polymerization initiation, or a water-containing gel-like crosslinked polymer obtained in the middle of polymerization or after polymerization (hereinafter, referred to as "hydrous gel"). Specifically, a polysaccharide such as starch or cellulose or a derivative thereof, polyvinyl alcohol, and the like can be incorporated in an amount of preferably 0% to 50% by weight, and more preferably 0.1% to 30% by weight. Such a graft polymer or a mixture with a polymer may be referred to as a water-absorbing resin composition, but in the present invention, the graft polymer or mixture may be referred to as a water-absorbing resin or a polyacrylic acid (salt)-type water-absorbing resin.

(Polymerization Method)

Polymerization according to the present invention is carried out by aqueous solution polymerization or reverse phase suspension polymerization from the viewpoint of the water absorption performance of the resulting particulate water-absorbing agent or the ease of polymerization control. These polymerization steps can be carried out in an atmosphere of air, but from the viewpoint of improving coloration of the particulate water-absorbing agent, the polymerization steps are preferably carried out in an atmosphere of an inert gas such as nitrogen or argon (for example, at an oxygen concentration of 1% by volume or less), and it is also preferable that the dissolved oxygen in the monomer be sufficiently purged with an inert gas (for example, the dissolved oxygen content is less than 1 mg/L).

In the present invention, the monomer described above is preferably used in the state of a solution in water or a mixed solvent of water and a hydrophilic solvent, and is particularly preferably used as an aqueous solution. In this case, the monomer concentration is preferably 20% to 80% by weight, more preferably 30% to 70% by weight, still more preferably 35% to 65% by weight, and particularly preferably 40% to 60% by weight. Meanwhile, if the monomer concentration is too high, the absorption capacity tends to decrease, which is not preferable.

The aqueous solution polymerization is a method of polymerizing an aqueous monomer solution without using a dispersing solvent such as a hydrophobic organic solvent, and refers to the mode of polymerization disclosed in, for example, U.S. Pat. Nos. 4,625,001, 4,873,299, 4,286,082, 4,973,632, 4,985,518, 5,124,416, 5,250,640, 5,264,495, 5,145,906, and 5,380,808; and EP 0811636, 0955086, 0922717, 1178059, 1711541, and 1799721. Furthermore, the reverse phase suspension polymerization is a method of performing polymerization by suspending an aqueous monomer solution in a hydrophobic organic solvent, and refers to the mode of polymerization disclosed in, for example, U.S. Pat. Nos. 4,093,776, 4,367,323, 4,446,261, 4,683,274, and 5,244,735. Meanwhile, on the occasion of the polymerization of the present invention, the monomer, crosslinking agent, polymerization initiator, and other additives described in the Patent Literatures described above can also be used in the present invention.

(Polymerization Initiator)

The polymerization initiator used in the present invention is appropriately selected depending on the mode of polymerization, and is not particularly limited, but examples thereof include a photodegradable polymerization initiator, a thermally decomposable polymerization initiator, and a redox system polymerization initiator. The using amount of these polymerization initiators is preferably 0.0001% to 1% by mole, and more preferably 0.001% to 0.5% by mole, with respect to the monomer.

Examples of the photodegradable polymerization initiator include benzoin derivatives, benzyl derivatives, acetophenone derivatives, benzophenone derivatives, and azo compounds. Examples of the thermally decomposable polymerization initiator include persulfates such as sodium persulfate, potassium persulfate, and ammonium persulfate; peroxides such as hydrogen peroxide, t-butyl peroxide, and methyl ethyl ketone peroxide; and azo compounds such as azonitrile compounds, azoamidine compounds, cyclic azoamidine compounds, azoamide compounds, alkylazo compounds, 2,2'-azobis(2-amidinopropane) dihydrochloride, and 2,2'-azobis[2-(2-imidazolin-2-yl)propane]dihydrochloride. Examples of the redox system polymerization initiator include systems obtained by combining the persulfates or peroxides with reducing compounds such as L-ascorbic acid and sodium hydrogen sulfite. Also, a photodegradable polymerization initiator and a thermally decomposable polymerization initiator can be used in combination.

(Surfactant, Dispersant)

In the present invention, a surfactant or a dispersant, such as an anionic surfactant, a nonionic surfactant, a cationic surfactant, or an amphoteric surfactant can be used at the time of polymerization. There are no particular limitations on these surfactants and dispersants; however, examples of the anionic surfactant include mixed fatty acid sodium soap, sodium fatty acids such as sodium stearate, sodium higher alcohol sulfate, sodium alkyl sulfate, and alkylbenzenesulfonic acid salts. Examples of the nonionic surfactant include polyoxyethylene alkyl ethers such as polyoxyethylene higher alcohol ethers, sorbitan fatty acid esters, and glycerin fatty acid esters; and examples of the cationic surfactant and amphoteric surfactant include alkylamines and alkyl betaines. Furthermore, examples of the dispersant include ethyl cellulose, and ethyl hydroxyethyl cellulose.

The using amount of the surfactant or dispersant is appropriately determined depending on the mode of polymerization, but generally, the using amount is preferably 1 part to 30 parts by weight, and more preferably 3 parts to 5 parts by weight, relative to 100 parts by weight of the total monomer components composed of polymerizable monomers and crosslinkable monomers.

(Organic Solvent in Reverse Phase Suspension Polymerization)

When the reverse phase suspension polymerization is carried out, the organic solvent used therefor is sparingly water-soluble and is not particularly limited as long as it is inert to polymerization, but examples of the organic solvent include aliphatic hydrocarbons such as n-pentane, n-hexane, n-heptane and n-octane; alicyclic hydrocarbons such as cyclohexane and methylcyclohexane; and aromatic hydrocarbons such as benzene, toluene and xylene. Among these, from the viewpoints of stability in industrial availability and product quality, n-hexane, n-heptane, and cyclohexane are particularly preferred. The using amount of these organic solvents is preferably 0.5 to 10 times by weight, and more preferably 0.6 to 5 times by weight, with respect to the aqueous solution of polymerizable monomers.

(2-2) Gel Fine Granulation Step

The hydrous gel obtained in the polymerization step can be subjected to drying in the form as received, but in the case of water solution polymerization, it is preferable that gel crushing of a hydrous gel obtained in the middle of polymerization or after polymerization be achieved by using a gel crusher (a kneader, a meat chopper, or the like) or the like, and the finely granulated hydrous gel (hereinafter, also referred to as "particulate hydrous gel") be dried. At this time, the hydrous gel is finely granulated according to a predetermined method, into fragments having a mass median particle size (D50) (defined by wet sieve classification) of preferably 0.1 mm to 50 mm, more preferably 0.2 mm to 10 mm, and still more preferably 0.5 mm to 5 mm. Meanwhile, the shape of the water-absorbing resin that is used in the particulate water-absorbing agent of the present invention is not particularly limited, and the water-absorbing resin can be produced into any arbitrary shape such as, for example, a granular form, a powder form, a flake form, or a fiber form. Furthermore, fine granulation can be carried out by various methods, but for example, a method of gel crushing the resin by using a screw type extruder having a porous structure with an arbitrary shape, may be used.

(2-3) Drying Step

The present step is a step for drying the hydrous gel or particulate hydrous gel that is obtained in the polymerization step or gel fine granulation step, and obtaining a dry polymer. The drying method is not particularly limited, but various methods such as, for example, drying by heating, drying by hot air, drying under reduced pressure, drying on a fluidized bed, drying by infrared, drying by microwave, drying by a drum dryer, dehydration by azeotropic boiling with a hydrophobic organic solvent, and high humidity drying using high temperature steam, may be used. Among these, drying by contact with a gas having a boiling point of preferably 40° C. to 100° C., and more preferably 50° C. to 90° C., is preferable.

In the drying step according to the present invention, the drying temperature is not particularly limited, but for example, the drying temperature is preferably 50° C. to 300° C., and from the viewpoint of enhancing the absorption capacity, the drying temperature is more preferably 100° C. to 250° C., still more preferably 120° C. to 230° C., and particularly preferably 150° C. to 200° C. Meanwhile, when the drying temperature is 100° C. or lower, azeotropic dehydration or drying under reduced pressure is preferred. Furthermore, the drying time is also appropriately determined and is not particularly limited, but for example, the drying time is preferably 10 seconds to 5 hours, and more preferably 1 minute to 2 hours.

Furthermore, when the mode of polymerization of the present invention is aqueous solution polymerization, from the viewpoints of the physical properties of the resulting particulate water-absorbing agent or the ease of pulverization, it is preferable that drying being achieved until the solids content of the dry polymer (water-absorbing resin) obtained after drying (defined in (6-8) Moisture content) reaches preferably 80% by weight or greater, more preferably 85% by weight or greater, still more preferably 90% by weight or greater, and particularly preferably 92% to 98% by weight. Thereafter, it is preferable that the polymer be further surface-crosslinked.

Furthermore, when the mode of polymerization of the present invention is reverse phase suspension polymerization, the hydrous gel obtainable during polymerization or after polymerization is such that for example, when azeotropic dehydration is carried out in a state in which the hydrous gel is dispersed in an organic solvent such as a hydrocarbon, the solids content becomes 60% by weight or greater, preferably 70% by weight or greater, more preferably 80% by weight or greater, still more preferably 85% by weight or greater, still more preferably 90% by weight or greater, particularly preferably 92% to 98% by weight, and most preferably 93% to 97% by weight. Furthermore, in the reverse phase suspension polymerization, it is preferable that surface-crosslinking be achieved in the middle of the drying step (for example, the solids content is 60% to 90% by weight). Meanwhile, after the drying, the product may be separated from the organic solvent by decantation or evaporation, and may be further dried as necessary.

(2-4) Pulverization Step and Classification Step

The present step is a step for pulverizing as necessary the dry polymer (dried product of the hydrous gel) obtained in the drying step (pulverization step), controlling the particle size by further classification (classification step), and obtaining water-absorbing resin particles. In regard to the pulverization or classification, for example, the methods disclosed in WO 2004/69915 can be employed.

From the viewpoint of enhancing the absorption against pressure (AAP) or the vertical diffusion absorption amount under pressure (VDAUP), it is preferable that the water-absorbing resin particles (water-absorbing resin obtained before surface-crosslinking) be controlled to a particle size in a specific range by pulverization, classification, or compounding after classification. For example, the mass median particle size (D50) is preferably 200 µm to 600 µm, more preferably 250 µm to 550 µm, and still more preferably 350 µm to 500 µm. Furthermore, the logarithmic standard deviation ($\sigma\zeta$) of the particle size distribution is preferably 0.20 to 0.50, more preferably 0.25 to 0.45, still more preferably 0.28 to 0.43, and particularly preferably 0.30 to 0.35. It is more desirable if the proportion of coarse particles having a particle size of 850 µm or greater (defined with a JIS standard sieve) is smaller, and the proportion is usually 0% to 5% by weight, preferably 0% to 3% by weight, and more preferably 0% to 1% by weight. It is also preferable if the proportion of fine particles having a particle size of less than 150 µm (defined with a JIS standard sieve) is smaller, and the proportion is usually 0% to 5% by weight, preferably 0% to 3% by weight, and more preferably 0% to 1% by weight. Furthermore, the bulk specific gravity (defined in U.S. Pat. No. 6,562,879) of the water-absorbing resin particles is preferably 0.30 to 0.90, more preferably 0.60 to 0.80, and still more preferably 0.65 to 0.75.

The particle size (mass median particle size (D50), logarithmic standard deviation ($\sigma\zeta$), and proportion of coarse particles or fine particles) or the bulk specific gravity described above are preferably applied to the water-absorbing resin particles, but are also preferably applied to the water-absorbing resin obtained after surface-crosslinking or the final particulate water-absorbing agent. When the particle size is not in the range described above, a decrease in the absorption against pressure (AAP) or the vertical diffusion absorption amount under pressure (VDAUP), or an increase in the re-wet amount (re-wet) in a disposable diaper is observed, which is therefore not preferable.

Accordingly, the control of the particle size or bulk specific gravity in the water-absorbing resin after surface-crosslinking or the final particulate water-absorbing agent is preferably carried out with the water-absorbing resin particles (water-absorbing resin before surface-crosslinking). Furthermore, if necessary, it is preferable that the water-absorbing resin obtained after surface-crosslinking or the final particulate water-absorbing agent be controlled to a particle size in a specific range by classification or compounding after classification.

(Physical Properties of Water-Absorbing Resin Particles)

In the present invention, the absorption capacity or the water-extractable of the water-absorbing resin particles (water-absorbing resin before surface-crosslinking) are controlled by appropriately setting the polymerization conditions (amount or species of the crosslinking agent, polymerization concentration, and the like), drying conditions or the like. However, since the relevant water-absorbing resin particles contain a small amount of water (for example, when the solids content of the water-absorbing resin particles is 93% to 97% by weight, the moisture content is 3% to 7% by weight) or the like even after drying, the amount of the water-absorbing resin in a sample may vary, and even in the same sample, when the moisture content changes as a result of heating or the like, the absorption capacity also changes.

That is, since the relevant absorption capacity ([g/g]) is defined by the weight [g] of the hydrous gel obtained after swelling with respect to the weight [g] of the water-absorbing resin particles, as the moisture content of the water-absorbing resin particles increases, the amount of the water-absorbing resin substantially decreases. Therefore, the absorption capacity apparently decreases.

Thus, in order to exclude the influence of the amount of water in the water-absorbing resin particles, so-called solids content compensation, by which the moisture content is normalized with respect to water-absorbing resin particles having a moisture content ratio of 0% by weight, is carried out. The solids content compensation is essential when the moisture content ratio is greater than 10% by weight, and even greater than 8% by weight, and it is still preferable to carry out the solids content compensation at a moisture content ratio of 8% by weight or less. The value obtained by solids content compensation is obtained by dividing the centrifuge retention capacity (CRC) obtained by the method described in section (6-1) by the solids content. Meanwhile, as described in section (6-8), the solids content and the moisture content ratio are defined by the weight loss on drying, which is obtained by drying 1 g of water-absorbing resin particles for 3 hours at 180° C.

When the solids content compensation is carried out before and after the surface crosslinking, the centrifuge retention capacity (CRC) of the water-absorbing resin particles obtained before the surface crosslinking is controlled to, as a value obtainable after the solids content compensation, 40 to 56 [g/g], preferably 40 to 55 [g/g], and more preferably 41 to 53 [g/g]. Meanwhile, when the moisture content ratio obtainable before and after the surface crosslinking is not in the range described above, particularly when the solids content of the water-absorbing resin particles before the surface crosslinking is 90% by weight or greater, since the moisture content ratio is less than 10% by weight, the influence on the CRC is decreased, and therefore, the solids content compensation may not be carried out. If the solids content compensation is not carried out, the centrifuge retention capacity (CRC) of the water-absorbing resin particles obtained before the surface crosslinking is controlled to 39 to 56 [g/g], preferably 39 to 55 [g/g], more preferably 39 to 53 [g/g], still more preferably 40 to 52 [g/g], and particularly preferably 41 to 50 [g/g].

Furthermore, while the cases where solids content compensation is carried out, such as in the case where the change amount of the moisture content described above exceeds 10% by weight, are also applied, the water-extractable (Ext) of the water-absorbing resin particles is preferably 1% to 60% by weight, more preferably 5% to 40% by weight, still more preferably 5% to 30% by weight, and particularly preferably 5% to 20% by weight. If the water-extractable (Ext) is high, the particulate water-absorbing agent of the present invention may not be obtained, and if the water-extractable is low, the water-absorbing resin particles have poor durability and the like.

Meanwhile, in regard to the production method of the present invention, as described above, it is necessary to control the centrifuge retention capacity (CRC) obtainable after the solids content compensation of the water-absorbing resin particles to 40 to 56 [g/g]. In order to do so, (1) amount of the crosslinking agent, (2) monomer concentration at the time of polymerization, (3) use of a chain transfer agent at the time of polymerization, (4) polymerization temperature, and (5) drying temperature may be appropriately set to the ranges indicated in the following items (1) to (5), respectively, and thus the centrifuge retention capacity (CRC) may be adjusted. Meanwhile, the items (1) to (5) are not to be limited to be used alone, and any plural conditions may be used in appropriate combination. (1) The amount of the crosslinking agent is used in an amount of preferably 0% to 5% by mole, more preferably 0.001% to 2% by mole, and still more preferably 0.005% to 1% by mole, relative to the amount of the monomers described above. Furthermore, the amount of the crosslinking agent is more preferably 0.01% to 0.1% by mole, particularly preferably 0.02% to 0.06% by mole, and most preferably 0.022% to 0.058% by mole, relative to the amount of the monomers described above. (2) The monomer concentration in the aqueous monomer solution is preferably 20% to 80% by weight, more preferably 30% to 70% by weight, still more preferably 35% to 65% by weight, and particularly preferably 40% to 60% by weight. (3) The chain transfer agent is used in an amount of preferably 0% to 5% by weight, more preferably 0% to 1% by weight, still more preferably 0.001% to 0.8% by weight, relative to the amount of the monomers described above. (4) The temperature of the aqueous monomer solution in the polymerization step is preferably set to 10° C. to 150° C., more preferably 30° C. to 130° C., still more preferably 50° C. to 120° C., and particularly preferably 80° C. to 110° C. (5) The drying temperature in the drying step is preferably set to 100° C. to 250° C., more preferably 120° C. to 230° C., and still more preferably 150° C. to 200° C.

Meanwhile, in regard to the items (1) to (5) described above, if the amount of the crosslinking agent is too small, the monomer concentration is less than 20% by weight, the amount of the chain transfer agent is greater than 5% by weight, the temperature of the aqueous monomer solution is higher than 150° C., and the drying temperature is higher than 250° C., the centrifuge retention capacity (CRC) of the water-absorbing resin particles obtainable before surface crosslinking becomes excessively high. As a result, the burden in the surface-crosslinking step increases, causing a decrease in the production efficiency, or all the performances of the free swell capacity (FSC), the absorption against pressure (AAP), and the vertical diffusion absorption amount under pressure (VDAUP) increase. Thus, there is a risk that a water-absorbing agent which is poorly balanced in these performances may be obtained, which is not preferable.

On the other hand, in regard to the items (1) to (5) described above, if the amount of the crosslinking agent is too high, the monomer concentration is greater than 80% by weight, the temperature of the aqueous monomer solution is lower than 10° C., and the drying temperature is lower than 100° C., since the centrifuge retention capacity (CRC) of the water-absorbing resin particles obtainable before surface crosslinking becomes excessively low. Therefore, there is a possibility that the performance of the particulate water-absorbing agent obtainable by the surface crosslinking step may deteriorate, and also, there is a risk that there may be a decrease in productivity, such as in the case where the control of the polymerization reaction may become difficult, or the time taken in the polymerization step or the drying step may become too long, which is not preferable.

(2-5) Surface Crosslinking Step

The present step is a step for surface-crosslinking the water-absorbing resin particles obtained in the pulverization step and classification step described above, and increasing the absorption against pressure (AAP) of the resulting water-absorbing resin. The particulate water-absorbing agent of the present invention is preferably a product formed as a polyacrylic acid (salt)-type water-absorbing resin is surface-crosslinked by a surface crosslinking agent other than a polycation. Meanwhile, the term "surface-crosslinking" means that the surface or the surface vicinity of water-absorbing resin particles is crosslinked, and the term "surface or surface vicinity" usually means the top layer portion having a thickness of several ten micrometers (μm) or less, or the top layer portion having a thickness corresponding to 1/10 or less of the total thickness, but these thicknesses are appropriately determined in accordance with the purpose. Furthermore, the water-absorbing resin used in the particulate water-absorbing agent of the present invention is obtained by surface-crosslinking the water-absorbing resin particles obtained in the steps (2-1) to (2-4) described above.

There are no particular limitations on the method for surface-crosslinking, but for example, a method of polymerizing a monomer at the surface of the water-absorbing resin particles, or a method of radical-crosslinking the surface of the water-absorbing resin particles by using a polymerization initiator (for example, a persulfuric acid salt) may be used. However, a method of crosslinking the surface of the water-absorbing resin particles by using a surface crosslinking agent is particularly preferred. In this case, the method is composed of a step for mixing with a surface crosslinking agent, a step for heat treating the mixture, and optionally a step for cooling the product.

(Surface Crosslinking Agent)

There are no particular limitations on the surface crosslinking agent used in the present invention, and examples thereof include oxazoline compounds (U.S. Pat. No. 6,297,319), vinyl ether compounds (U.S. Pat. No. 6,372,852), epoxy compounds (U.S. Pat. No. 6,265,488), oxetane compounds (U.S. Pat. No. 6,809,158), polyhydric alcohol compounds (U.S. Pat. No. 4,734,478), polyamide polyamine-epihalo adducts (U.S. Pat. Nos. 4,755,562 and 4,824,901), hydroxyacrylamide compounds (U.S. Pat. No. 6,239,230), oxazolidinone compounds (U.S. Pat. No. 6,559,239), bis- or polyoxazolidinone compounds (U.S. Pat. No. 6,472,478), 2-oxotetrahydro-1,3-oxazolidine compounds (U.S. Pat. No. 6,657,015), and alkylene carbonate compounds (U.S. Pat. No. 5,672,633), and one kind or two or more kinds of these are used. Furthermore, these surface crosslinking agents and water-soluble polyvalent metal cations such as aluminum salts (U.S. Pat. Nos. 6,605,673 and 6,620,899) may be used in combination, or these surface crosslinking agents and alkali metal salts (US 2004/106745), organic acids or inorganic acids (U.S. Pat. No. 5,610,208), and the like may also be used in combination. Furthermore, it is also acceptable to carry out polymerization of monomers at the surface of the water-absorbing resin and to perform surface-crosslinking (US 2005/48221).

Among these, organic surface crosslinking agents, particularly covalent-bond-forming surface crosslinking agents are preferably used, and specifically, one kind or two or more kinds of polyhydric alcohol compounds, polyvalent epoxy compounds, polyvalent amine compounds or salts thereof, and alkylene carbonate compounds are preferred. Since these generally hydrophilize the surface, the production method of the present invention can be effectively applied.

Specific examples of the surface crosslinking agent include polyhydric alcohol compounds such as (di-, tri-, tetra-, poly-)ethylene glycol, (di-, poly-)propyleneglycol, 1,3-propanediol, 2,2,4-trimethyl-1,3-pentanediol, (poly)glycerin, 2-butene-1,4-diol, 1,4-butanediol, 1,3-butanediol, 1,5-pentanediol, 1,6-hexanediol, trimethylolpropane, di-or-triethanolamine, pentaerythritol, and sorbitol; epoxy compounds such as (poly)ethylene glycol diglycidyl ether, (di-, poly-)glycerol polyglycidyl ether, (di-, poly-)propylene glycol diglycidyl ether, and glycidol; polyvalent oxazoline compounds such as 1,2-ethylenebisoxazoline; alkylene carbonate compounds such as 1,3-dioxolan-2-one; monooxazolidinone compounds such as 2-oxazolidinone, or polyvalent oxazolidinone compounds; oxetane compounds, and polyvalent metal compounds containing water-soluble polyvalent metal cations, such as aluminum sulfate. These surface crosslinking agents may be used singly, or two or more kinds may be used in combination.

Among these surface-crosslinking agents, from the viewpoint of physical properties, a dehydration-reactive surface crosslinking agent selected from polyhydric alcohol compounds alkylene carbonate compounds, oxazolidinone compounds, and oxetane compounds is preferred, and it is particularly preferable that one or more kinds of polyhydric alcohol compounds, alkylene carbonate compounds and oxazolidinone compounds be used, and optionally another surface crosslinking agent be used. Meanwhile, here, the dehydration-reactive surface crosslinking agent refers to a crosslinking agent which crosslinks with a carboxyl group of a polyacrylic acid (salt) by a dehydration reaction. Examples of the surface crosslinking agent other than the dehydration-reactive surface crosslinking agent include ion-reactive surface crosslinking agents such as polyvalent metal salts, and ring-opening-reactive surface crosslinking agents such as epoxy compound crosslinking agents, and these surface crosslinking agents may be used singly or in combination.

The using amount of the surface crosslinking agent is preferably 0.01 parts to 10 parts by weight, more preferably 0.3 parts to 8 parts by weight, and still more preferably 0.5 parts to 5 parts by weight, relative to 100 parts by weight of the water-absorbing resin. If the using amount of the surface crosslinking agent is less than 0.01 parts by weight, there is a risk that liquid permeability may decrease. Furthermore, if the using amount is greater than 10 parts by weight, there is a risk that the absorption capacity may drastically decrease, which is not preferable. Meanwhile, the using amount of the surface crosslinking agent means the total amount in the case where two or more kinds of surface crosslinking agents are used in combination.

In the present invention, it is preferable that a hydrophilic organic compound such as a polyhydric alcohol compound be further incorporated into the surface of the water-absorbing resin. In this case, the hydrophilic organic compound is incorporated in an amount of preferably 0.001 parts to 10 parts by weight, more preferably 0.005 parts to 5 parts by weight, and still more preferably 0.01 parts to 3 parts by weight, relative to 100 parts by weight of the water-absorbing resin. Meanwhile, the hydrophilic organic compound refers to an organic compound which dissolves in an amount of 1 g or more, and preferably 10 g or more, in 100 g of water at normal temperature.

(Solvent)

At the time of mixing the water-absorbing resin particles with a surface crosslinking agent, the surface crosslinking agent may be mixed alone, but it is preferable to mix the surface crosslinking agent in the form of a solution, and it is preferable to use water in particular as the solvent. When the total using amount of water is 1 part to 10 parts by weight relative to 100 parts by weight of the water-absorbing resin particles, the aqueous solution of surface crosslinking agent sufficiently penetrates to the surface of the water-absorbing resin, and a multilayered surface-crosslinked layer having appropriate thickness and density is formed.

Furthermore, at the time of mixing the water-absorbing resin particles and the surface crosslinking agent, if necessary, a hydrophilic organic solvent may be used as a solvent. Examples of the hydrophilic organic solvent include lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane, tetrahydrofuran, and alkoxypolyethylene glycol; amides such as N,N-dimethylformamide; and sulfoxides such as dimethyl sulfoxide. The using amount of the hydrophilic organic solvent may vary with the type or particle size of the water-absorbing resin particles, but the using amount is preferably 20 parts by weight or less, and more preferably in the range of 0.1 parts to 10 parts by weight, relative to 100 parts by weight of the solids content of the water-absorbing resin particles.

(Surface Crosslinking Method)

There are no particular limitations on the method of mixing the water-absorbing resin particles and the surface crosslinking agent, but a method of mixing a surface crosslinking agent that has been dissolved in water and/or a hydrophilic organic solvent, with the water-absorbing resin particles directly, by spraying, or by adding dropwise, is preferred.

The mixing apparatus used when the water-absorbing resin particles and the surface crosslinking agent are mixed, preferably has a high mixing power in order to mix the two components uniformly and reliably. There are no particular limitations on the mixing apparatus, but examples thereof include a cylindrical mixer, a double-walled conical mixer, a V-type mixer, a ribbon type mixer, a screw type mixer, a flow type furnace rotary disc type mixer, an air flow type mixer, a double-blade type kneader, an internal mixer, a pulverizing type kneader, a rotary mixer, a screw type extruder, and a turbulizer.

When the water-absorbing resin particles and the crosslinking agent are mixed, the temperature is, as the temperature of the water-absorbing resin particles, the aqueous solution of surface crosslinking agent, and a mixture thereof, preferably 10° C. to 200° C., and more preferably 20° C. to 100° C. Furthermore, the mixing time is preferably 1 second to 1 hour, and more preferably 5 seconds to 10 minutes.

The mixture of the water-absorbing resin particles and the surface crosslinking agent is preferably heated for the crosslinking reaction. The heating temperature may be appropriately selected, but the heat medium temperature is preferably in the range of 150° C. to 250° C., and more preferably 180° C. to 210° C. Furthermore, the heating time is preferably 1 minute to 2 hours, and suitable examples of the combination of the heating temperature and the heating time include 0.1 hours to 1.5 hours at 180° C., 0.1 hours to 1 hour at 200° C., 30 minutes to 50 minutes at 210° C., and 30 to 60 minutes at 215° C.

When the mixture of the water-absorbing resin particles and the surface crosslinking agent is heated, the mixture may be heated in a static state, or may be heated by using a mixing means such as stirring. However, from the viewpoint that the entirety of the mixture can be uniformly heated, it is preferable to heat the mixture while the mixture is stirred and mixed.

When the surface crosslinking step described above is carried out, the production can be controlled so as to obtain water-absorbing resin particles having an centrifuge retention capacity (CRC) of 32 to 40 [g/g], preferably 32 to 38 [g/g], and more preferably 33 to 36 [g/g].

Furthermore, when such a surface crosslinking step is carried out, the production can be controlled so as to obtain water-absorbing resin particles having an absorption against pressure (AAP—4.83 kPa) of 20 to 30 [g/g], more preferably 20 to 29 [g/g], and still more preferably 21 to 29 [g/g].

(Preferred Surface Crosslinking Method)

A method of surface crosslinking which is preferable for obtaining the particulate water-absorbing agent of the present invention will be described below.

It is conventionally known that when a surface crosslinking treatment is applied, the absorption against pressure (for example, AAP) or liquid permeability (for example, SFC) increases, while the absorption capacity without load (for example, CRC) decreases. That is, since the centrifuge retention capacity and particularly liquid permeability are contradictory performances, in the conventional methods for producing a water-absorbing agent, it has been very difficult to obtain these performances all at a high level in a well-balanced manner. In contrast to this, the particulate water-absorbing agent obtainable by the present invention does not sacrifice the absorption capacity under no added pressure, and the present invention provides a method for producing a particulate water-absorbing agent having a high absorption against pressure and high liquid permeability in a well-balanced manner.

In order to achieve the objects described above, first, as step (A), it is needed to obtain water-absorbing resin particles having an centrifuge retention capacity (CRC) of 40 to 56 [g/g] before surface crosslinking, and the methods described above can be employed. Meanwhile, a preferred range of the centrifuge retention capacity (CRC) of the water-absorbing resin particles obtainable in step (A) is mentioned in the section (Physical properties of water-absorbing resin particles) of (2-4) Pulverization step and classification step.

Subsequently, as step (B), it is needed to surface-crosslink the water-absorbing resin particles obtained in step (A), and to obtain a water-absorbing resin powder having an centrifuge retention capacity (CRC) of 32 to 40 [g/g] and an absorption against pressure (AAP—4.83 kPa) of 20 to 30 [g/g]. Meanwhile, the centrifuge retention capacity (CRC) of the water-absorbing resin powder obtainable in step (B) is 32 to 40 [g/g], preferably 32 to 39 [g/g], and more preferably 33 to 38 [g/g]. Furthermore, the absorption against pressure (AAP—4.83 kPa) is 20 to 30 [g/g], preferably 20 to 29 [g/g], and more preferably 21 to 29 [g/g].

Furthermore, as a production method for obtaining the particulate water-absorbing agent related to the present invention, in step (B), the relation between the centrifuge retention capacity (CRC) obtained before and after surface crosslinking, that is, the decrement of the absorption capacity defined by the following formula, is preferably 7 [g/g] or greater, and more preferably 16 [g/g] or less. That is, it is preferable that the decrement of the absorption capacity satisfy 7 to 16 [g/g]. Furthermore, the decrement of the absorption capacity is more preferably 8 to 15 [g/g], and still more preferably 8 to 14 [g/g]. When the decrement of the absorption capacities obtained before and after surface crosslinking is 7 to 16 [g/g], the surface-crosslinking strength is sufficiently high, and a particulate water-absorbing agent of the present invention which is excellently balanced between the free swell capacity (FSC), the absorption against pressure (AAP), and the vertical diffusion absorption amount under pressure (VDAUP), can be obtained.

Decrement of absorption capacity [g/g]={Centrifuge retention capacity (CRC) before surface crosslinking}−{centrifuge retention capacity (CRC) after surface crosslinking}  [Mathematical Formula 1]

Regarding a specific means of control, for example, when the centrifuge retention capacity (CRC) of the water-absorbing resin particles obtainable before surface crosslinking is 39 to 41 [g/g], it is preferable to set the heating temperature at the time of surface crosslinking to 150° C. to 210° C., and the heating time to 0.1 hours to 1.0 hour. When the centrifuge retention capacity (CRC) of the water-absorbing resin particles obtainable before surface crosslinking is greater than 41 [g/g] and less than 53 [g/g], it is preferable to set the heating temperature at the time of surface crosslinking to 150° C. to 230° C., and the heating time to 0.2 hours to 1.5 hours. Furthermore, for example, when the centrifuge retention capacity (CRC) of the water-absorbing resin particles obtainable before surface crosslinking is 53 to 56 [g/g], it is preferable to set the heating temperature at the time of surface crosslinking to 180° C. to 250° C., and the heating time to 0.5 hours to 1.8 hours. Meanwhile, when the change in the solids content of the water-absorbing resin before and after surface crosslinking is considered, it is preferable that both the centrifuge retention capacity (CRC) and the absorption against pressure (AAP—4.83 kPa) be indicated by values that have been obtained by solids content compensation.

Meanwhile, the moisture content ratio obtainable after surface crosslinking is appropriately determined in accordance with the moisture content ratio of the water-absorbing resin particles obtainable before surface crosslinking, the type of the surface crosslinking agent, the reaction temperature and time, and the like, but the moisture content ratio is preferably in the range of 0% to 15% by weight, more preferably 0.5% to 10% by weight, and still more preferably 0.6% to 3% by weight. In general, since the dehydrating surface crosslinking agent described above needs dehydration, the water-absorbing resin obtainable after surface crosslinking becomes a water-absorbing resin with a low moisture content ratio (for example, 0% to 3% by weight). Also, since dehydration is optional in an ion-reactive surface crosslinking agent or a ring-opening-reactive surface crosslinking agent, it is also possible to maintain the moisture content ratio high. These moisture content ratios may be appropriately controlled in accordance with the purpose.

(2-6) Spacer Addition Step (Step for Producing Particulate Water Absorbent)

The method for producing a particulate water-absorbing agent related to the present invention is characterized in that the centrifuge retention capacity (CRC) is controlled to the range described above before and after surface crosslinking (specifically, water-absorbing resin particles having a CRC of 40 to 56 [g/g] are surface-crosslinked until the CRC becomes 32 to 40 [g/g]), and then a trace amount of a particular spacer is incorporated.

The term "spacer" according to the present invention refers to a compound having a property in which when the spacer is caused to exist on the surface of a water-absorbing resin, particularly in the state of a gel that has absorbed an aqueous liquid and swollen, the distances between particles can be extended sterically or eletrostatically. Usually, since swollen gel particles are such that particularly the contact area between the particles are enlarged under pressure and the intervals are decreased, the amount of liquid that can be retained between the gel particles is decreased, or liquid diffusibility or liquid permeability between swollen gel layers can be interrupted. Thus, in the present invention, the amount of liquid retained between gel particles can be increased by mixing the spacer that will be described below with the water-absorbing resin, and the liquid diffusibility or liquid permeability between the gel layers can be further increased. Consequently, the absolute absorption amount into paper diapers can be maximized.

The spacer used in the present invention is preferably such that the decrement of the absorption against pressure (AAP) is 5.0 [g/g] or less. Furthermore, it is preferable to use the spacer in an amount and a type that give a decrement of the absorption against pressure of preferably 3.0 [g/g] or less, more preferably 2.5 [g/g] or less, still more preferably 2.0 [g/g] or less, particularly preferably 1.5 [g/g] or less, and most preferably 0.5 [g/g] or less. Meanwhile, the lower limit of the decrement is 0 [g/g] (that is, there is no decrease in the AAP) or −1 [g/g] (that is, the AAP increases by +1). When the absorption against pressure (AAP) is decreased in the range described above, the vertical diffusion absorption amount under pressure (VDAUP) can be increased to an intended range, and the free swell capacity (FSC) can be increased.

Specific examples of such a spacer include water-insoluble fine particles (steric spacers); and polycations, particularly polyvalent metal cations and polyvalent cationic polymers (electrostatic spacers).

In the present invention, it was found that when a spacer, particularly water-insoluble fine particles, a polyvalent metal cation or a polyvalent cationic polymer is added to a water-absorbing resin that has been subjected to surface crosslinking until an centrifuge retention capacity (CRC) in the aforementioned particular range is obtained, a slight decrease in the absorption against pressure (AAP) can be seen; however, the free swell capacity (FSC) increases to a large extent, and consequently, the absolute absorption amount and the re-wet amount in a disposable diaper are significantly improved. Meanwhile, if a spacer with which the absorption against pressure (AAP) does not decrease is used, there is no, or if any, insufficient, improvement in the absolute absorption amount or the re-wet amount in a disposable diaper. Furthermore, if the absorption against pressure (AAP) decreases excessively, the water absorption performance in a disposable diaper also decreases, which is not preferable.

Conventionally, the absorption against pressure (AAP) has been emphasized in water-absorbing agents for paper diaper applications. However, the particulate water-absorbing agent of the present invention is such that although the absorption against pressure (AAP) is slightly sacrificed, the free swell capacity (FSC) drastically increases, and consequently, the absolute absorption amount and the re-wet amount in a disposable diaper increased to a large extent.

The particulate water-absorbing agent related to the present invention contains, as a spacer, at least one or more spacers selected from polycations and water-insoluble fine particles. The polycations are selected from the group consisting of polyvalent metal cations and polyvalent cationic polymers. That is, in order to obtain a particulate water-absorbing agent related to the present invention, a polyvalent metal cation, a polyvalent cationic polymer, and water-insoluble fine particles are used as the spacer, respectively in specific amounts. Meanwhile, in the present invention, regarding the polyvalent metal cation, polyvalent cationic polymer, and water-insoluble fine particles, one kind may be added, or two or more kinds may be added. Furthermore, in the case of adding two or more kinds thereof, two or more kinds may be added simultaneously, or one kind may be added first, and then another one kind or two or more kinds may be further added.

Specifically, a first production method may be a method of controlling the centrifuge retention capacity (CRC) obtainable before and after surface crosslinking to the aforementioned ranges, and then mixing the surface-crosslinked water-absorbing resin and a spacer in amounts which result in a decrement of the absorption against pressure (AAP) of 3 [g/g] or less; a second production method may be a method of controlling the centrifuge retention capacity (CRC) obtainable before and after surface crosslinking to the aforementioned ranges, and then mixing 0.001 parts to 3 parts by weight of a polyvalent metal cation in the form of an aqueous solution, with 100 parts by weight of the surface-crosslinked water-absorbing resin; a third production method may be a method of controlling the centrifuge retention capacity (CRC) obtainable before and after surface crosslinking to the aforementioned ranges, and then mixing 0.001 parts to 0.5 parts by weight of a polyamine polymer in the form of an aqueous solution or in an intact form, with 100 parts by weight of the surface-crosslinked water-absorbing resin; and a fourth production method may be a method of controlling the centrifuge retention capacity (CRC) obtainable before and after surface crosslinking to the aforementioned ranges, and then directly mixing 0.001 parts to 0.4 parts by weight of water-insoluble fine particles with 100 parts by weight of the surface-crosslinked water-absorbing resin.

In the first to fourth production methods described above, the absorption against pressure (AAP) of the water-absorbing resin obtainable after surface crosslinking is 20 to 30 [g/g], and the absorption against pressure (AAP) of the water-absorbing resin particles obtainable before surface crosslinking is 15 [g/g] or less, and 5 to 12 [g/g]. Furthermore, the particle size of the water-absorbing resin suitable to control the absorption against pressure (AAP) or the vertical diffusion absorption amount under pressure (VDAUP) is in the range described above.

That is, in the production methods of the present invention, as the centrifuge retention capacity (CRC) obtainable before and after surface crosslinking is controlled to particular ranges, and the surface-crosslinked water-absorbing resin and a spacer are mixed, a particulate water-absorbing agent that is unprecedented, which is excellently balanced between the free swell capacity (FSC), the absorption against pressure (AAP), and the vertical diffusion absorption amount under pressure (VDAUP), can be obtained.

Furthermore, when the centrifuge retention capacity (CRC) obtainable before and after surface crosslinking is such that the decrement of the absorption capacity defined by the relationship formula of Mathematical formula (1) is 7 [g/g] or greater, the crosslinking density at the surface of the water-absorbing resin is increased, and the balance between the free swell capacity (FSC), the absorption against pressure (AAP), and the vertical diffusion absorption amount under pressure (VDAUP) can be improved.

Furthermore, when the centrifuge retention capacity (CRC) obtainable before and after surface crosslinking is such that the decrement of the absorption capacity defined by the relationship formula of Mathematical formula (I) is 16 [g/g] or less, an excessive crosslinking density at the surface of the water-absorbing resin is suppressed, and the balance between the free swell capacity (FSC), the absorption capacity under pressure (AAP), and the vertical diffusion absorption amount under pressure (VDAUP) can be improved.

Meanwhile, Patent Literatures 1 to 3 and 5 mentioned above disclose a technology of mixing a polyvalent metal cation with a water-absorbing resin obtained after surface crosslinking, and Patent Literature 4 mentioned above discloses a technology of defining the physical properties of a water-absorbing resin before a polyvalent metal cation is added. However, in these Patent Literatures, there is no disclosure of the technical idea of controlling the centrifuge retention capacity (CRC) obtainable before and after surface crosslinking, and there is also no disclosure purported to improve the balance between the free swell capacity (FSC), the absorption against pressure (AAP), and the vertical diffusion absorption amount under pressure (VDAUP). Therefore, the particulate water-absorbing agent of the present invention cannot be obtained by the methods disclosed in the Patent Literatures 1 to 5.

Furthermore, it was found that when the particulate water-absorbing agent related to the present invention is used as a disposable diaper, the final evaluation in the disposable diaper is correlated with a decrease in the absorption against pressure (AAP) caused by the addition of a spacer. That is, the actual use of a water-absorbing resin or a water-absorbing agent can be verified or anticipated even without performing an evaluation of a disposable diaper, which takes so much effort and time. From the findings described above, the particulate water-absorbing agent related to the present invention may be obtained.

(Spacer)
(a) Polyvalent Metal Cation

In the second production method of the present invention, the water-absorbing resin having particular CRC and AAP values is mixed with a small amount of a polyvalent metal cation. It was found that the polyvalent metal cation exists at the surface of the water-absorbing resin having particular CRC and AAP values, and acts as an electrostatic spacer between particles, thereby increasing the FSC and VDAUP of the particulate water-absorbing agent.

The polyvalent metal compound that can be used in the polyvalent metal cation in the present invention is preferably water-soluble (water-soluble polyvalent metal cation). Regarding the polyvalency, the polyvalent metal compound is essentially divalent or higher, and preferably divalent to tetravalent. Furthermore, a trivalent metal cation, particularly aluminum cation, is used.

The term water-soluble according to the present invention refers to a compound which is dissolved in an amount of 1 g or more, and preferably 10 g or more, in 100 g of water (25° C.). The polyvalent metal compound containing a polyvalent metal cation may be directly mixed (mainly in a solid state) with the water-absorbing resin particles, but from the viewpoint of increasing the FSC, it is preferable to use a water-soluble polyvalent metal compound and to mix an aqueous solution of this compound with the water-absorbing resin. When a water-soluble polyvalent metal compound is mixed in the state of an aqueous solution, the polyvalent metal cation generated when the polyvalent metal compound is dissociated acts as an electrostatic spacer between particles, and the water-absorbing agent of the present invention can be obtained more efficiently.

The polyvalent metal cation that can be used in the present invention preferably includes cations of at least one or more metals selected from typical metals and the transition metals of Groups 4 to 11. Among the polyvalent metals, the polyvalent metal cation preferably includes Mg, Ca, Ti, Zr, V, Cr, Mn, Fe, Co, Ni, Pd, Cu, Zn, Cd, and Al, and Mg, Ca, Zn and Al are more preferred, while Al is particularly preferred.

When the water-absorbing resin having a particular CRC value (32 to 40 [g/g]) and the polyvalent metal cation are mixed, the polyvalent metal compound containing the polyvalent metal cation that can be used in the present invention may be such that the counter anion may be either organic or inorganic, and is not particularly limited. Examples of the polyvalent metal compound include water-soluble aluminum salts such as aluminum acetate, aluminum lactate, aluminum acrylate, aluminum chloride, polyaluminum chloride, aluminum sulfate, aluminum nitrate, aluminum potassium bis(sulfate), and aluminum sodium bis(sulfate); water-soluble alkaline earth metal salts such as calcium chloride, calcium nitrate, magnesium chloride, magnesium sulfate, and magnesium nitrate; transition metal salts such as zinc chloride, zinc sulfate, zinc nitrate, copper sulfate, cobalt chloride, zirconium chloride, zirconium sulfate, and zirconium nitrate. Particularly preferred among these are aluminum compounds, and among others, aluminum sulfate is preferred. A powder of hydrous crystals of aluminum sulfate tetradecahydrate to octadecahydrate, or the like can be most suitably used.

In the case of using a polyvalent metal salt of an organic acid, preferred example of the anion include bases corresponding to acids, such as fatty acids such as anisic acid, benzoic acid, p-hydroxybenzoic acid, formic acid, valeric acid, citric acid, glycolic acid, glyceric acid, glutaric acid, chloroacetic acid, chloropropionic acid, cinnamic acid, succinic acid, acetic acid, tartaric acid, lactic acid, pyruvic acid, fumaric acid, propionic acid, 3-hydroxypropionic acid, malonic acid, maleic acid, butyric acid, isobutyric acid, imidinoacetic acid, malic acid, isothionic acid, methylmaleic acid, adipic acid, itaconic acid, crotonic acid, oxalic acid, salicylic acid, gluconic acid, gallic acid, sorbic acid, and stearic acid. Among these, tartaric acid salts and lactic acid salts are preferred, and lactates such as aluminum lactate and calcium lactate are most preferred.

In order to obtain an intended VDAUP value, the method for mixing the polyvalent metal cation may be such that the water-absorbing resin is mixed with an aqueous solution containing the polyvalent metal cation, particularly an aqueous solution having a polyvalent metal cation concentration of 1% to 60% by weight, and preferably 3% to 50% by weight, and after mixing, the mixture may be optionally heated at about 40° C. to 150° C., and preferably at 60° C. to 100° C. The using amount of water is preferably 0.1 parts to 5 parts by weight, and more preferably 0.5 parts to 3 parts by weight, relative to 100 parts by weight of the water-absorbing resin. More preferably, at the time of mixing, a polyhydric alcohol such as propanediol, glycerin or 1,4-butanediol, or an α-hydroxycarboxylic acid is used in combination. Meanwhile, the polyhydric alcohol is appropriately selected from the various compounds described above, and the α-hydroxycarboxylic acid will be described below. The polyhydric alcohol or α-hydroxycarboxylic acid is used in a smaller amount than that of water, and is preferably used in an amount of 0 parts to 4 parts by weight, 0.01 parts to 3 parts by weight, and 0.02 parts to 0.5 parts by weight, relative to 100 parts by weight of the water-absorbing resin.

The using amount of the polyvalent metal compound is, in terms of the polyvalent metal cation, preferably in the range of 0.001 parts to 3 parts by weight, more preferably in the range of 0.005 parts to 2 parts by weight, still more preferably in the range of 0.01 parts to 1 part by weight, still more preferably in the range of 0.02 parts to 0.9 parts by weight, particularly preferably in the range of 0.03 parts to 0.22 parts by weight, and most preferably in the range of 0.035 parts to 0.20 parts by weight, relative to 100 parts by weight of the water-absorbing resin particles. If the using amount of the polyvalent metal cation is smaller than 0.001 parts by weight relative to 100 parts by weight of the water-absorbing resin, the increase in the FSC is not sufficiently achieved. If the using amount of the polyvalent metal cation is larger than 3 parts by weight, there is a possibility that the AAP or VDAUP may be decreased by the mixing, to the extent that the present invention is not satisfied.

(b) Polyvalent Cationic Polymer

In the third production method of the present invention, the water-absorbing resin having particular CRC and AAP values is mixed with a small amount of a polyvalent cationic polymer. It was found that the polyvalent cationic polymer exists on the surface of particles of the water-absorbing resin having particular CRC and AAP values, and acts as an electrostatic spacer between the particles, thereby increasing the FSC and VDAUP values of the water-absorbing agent.

The polyvalent cationic polymer used in the present invention is preferably a polyamine polymer having a molecular weight of 1,000 or greater.

The polyvalent cationic polymer that can be used in the present invention preferably has a weight average molecular weight of 1,000 or greater, more preferably has a weight average molecular weight of 2,000 or greater, still more preferably has a weight average molecular weight of 5,000 or greater, and most preferably has a weight average molecular weight of 10,000 or greater. Furthermore, preferably, the number average molecular weight is 2,000 or greater, and more preferably, the number average molecular weight is 5,000 or greater. If the weight average molecular weight is less than 1,000, there is a risk that the expected effects may not be obtained. Meanwhile, the measurement of the average molecular weight is carried out such that the number average molecular weight is measured according to a viscosity method, and the weight average molecular weight is measured according to a sedimentation equilibrium method. In addition, the average molecular weight can also be measured by gel permeation chromatography, a static light scattering method, or the like. Meanwhile, in view of cost, a sufficient upper limit of the weight average molecular weight is about 5,000,000, and preferably about 1,000,000.

Furthermore, the polyvalent cationic polymer according to the present invention is such that the cation density is preferably 2 [mmol/g] or greater, more preferably 4 [mmol/g] or greater, and most preferably 6 [mmol/g] or greater. If the cation density is less than 2 [mmol/g], there is a risk that in a water-absorbing resin obtained by mixing a water-absorbing resin and a polyvalent cationic polymer, the shape retentivity of the water-absorbing resin aggregates obtained after swelling may not be sufficient. The upper limit is appropriately determined in accordance with the repeating unit, but the upper limit is 30 [mmol/g] or less, and preferably 25 [mmol/g] or less.

Specific examples of the polyvalent cationic polymer include cationic polymer electrolytes such as, for example, polyethyleneimine, a modified polyamidoamine modified by grafting of ethyleneimine, a protonated polyamidoamine, a condensate of polyamidoamine and epichlorohydrin, dimethylamine, a condensate of an amine such as ammonia and epichlorohydrin, poly(vinylbenzyldialkylammonium), poly(diallylalkylammonium), poly(2-hydroxy-3-methacryloyloxypropyldialkylamine), polyether amine, polyvinylamine, a modified polyvinylamine, a partial hydrolysate of poly(N-vinylformamide), a partial hydrolysate of poly(N-vinylalkylamide), a partial hydrolysate of a (N-vinylformamide)-(N-vinylalkylamide) copolymer, polyalkylamine, polyvinylimidazole, polyvinylpyridine, polyvinylimidazoline, polyvinyltetrahydropyridine, polydialkylaminoalkyl vinyl ether, polydialkylaminoalkyl (meth)acrylate, polyallylamine, polyamidine, a cationization product of starch or cellulose, salts thereof, and reaction products thereof with electrophilic reagents. Polyamidine as used herein is a polymer having an amidine ring in the molecule, and a product obtained by copolymerizing N-vinylformamide and acrylonitrile and then acid-treating the copolymer, is more preferred. Specific examples of the polyamidine include, but are not limited to, the cationic polymers having an amidine structure that are described in JP 2624089 A.

Among these, in view of the effects of the present invention, a polyamine polymer including at least one selected from polyamidine or a salt thereof, polyvinylamine or a salt thereof, a polyvinylamine-poly(N-vinylformamide) copolymer or a salt thereof, and a partial hydrolysate of poly(N-vinylformamide) or a salt thereof, and a polyamine polymer including polyvinylamine or a salt thereof, and a partial hydrolysate of poly(N-vinylformamide) or a salt thereof are suitable. Such a polyvalent cationic polymer may also contain another repeating unit at a proportion of about 0% to 30% by mole, and preferably 0% to 10% by mole. There are no particular limitations on the method of producing such a polyvalent cationic polymer, but particularly, in a method for hydrolyzing poly(N-vinylformamide), a polyvalent cationic polymer having an amine group and formic acid (salt) are produced. Using a mixture of this partial hydrolysate or a salt thereof and formic acid upon mixing thereof with the water-absorbing resin, is preferable from the viewpoint of simplification of the step, since the addition of the polyvalent cationic polymer and formic acid can be carried out simultaneously. Meanwhile, in the production of a partial hydrolysate of poly(N-vinylformamide), a purification method in which purification is not achieved so that a predetermined amount of formic acid remains, or formic acid is not excluded, must be employed.

The hydrolysis ratio of a partial hydrolysate of poly(N-vinylformamide) or a salt thereof is preferably 10% to 100% by mole, more preferably 20% to 95% by mole, and particularly preferably 30% to 90% by mole. Meanwhile, the hydrolysis ratio represents the proportion (%) of amine groups (mole number) obtained by hydrolysis, with respect to formamide groups (mole number) before hydrolysis. Here, a 100 mol % hydrolysate corresponds to polyvinylamine or a salt thereof.

Regarding the method of incorporating a polyvalent cationic polymer, the polyvalent cationic polymer may be directly incorporated into the water-absorbing resin, or the polyvalent cationic polymer may be incorporated as an aqueous solution. However, it is preferable to incorporate the polyvalent cationic polymer as an aqueous solution, particularly an aqueous solution having a concentration of the polyvalent cationic polymer of 1% to 60% by weight, and more preferably 10% to 50% by weight, and after mixing, the mixture may be optionally heated at about 40° C. to 150° C., and preferably at 60° C. to 100° C. In regard to the mixing machine or the heating treatment, the same apparatus as that used for surface crosslinking is appropriately selected and included. Meanwhile, the aqueous solution described above may contain an alcohol such as methanol, ethanol or isopropanol, and the amount of the alcohol is preferably 0.001 to 5 times by weight, more preferably 0.01 to 3 times by weight, and still more preferably 0.25 to 2.5 times by weight, relative to the amount of water. More preferably, a polyhydric alcohol such as propanediol, glycerin or 1,4-butanediol, or an α-hydroxycarboxylic acid is used in combination at the time of mixing. Meanwhile, the polyhydric alcohol is appropriately selected from the various compounds described above, and the α-hydroxycarboxylic acid will be described below. The polyhydric alcohol or α-hydroxycarboxylic acid is used in a smaller amount than that of water, and is preferably used in an amount of 0 parts to 4 parts by weight, 0.01 parts to 3 parts by weight, and preferably 0.02 parts to 0.5 parts by weight, relative to 100 parts by weight of the water-absorbing resin. Meanwhile, the α-hydroxycarboxylic acid used in the present invention will be described below.

The proportion of the water-absorbing resin and the polyvalent cationic polymer may be to such an extent that the absorption against pressure (AAP) or the VDAUP is not extremely decreased by the addition of the polyvalent cationic polymer, and particularly the decrease of AAP is 3.0 [g/g] or less. The amount of the polyvalent cationic polymer may be appropriately determined, but is preferably less than 0.3 parts by weight, 0.25 parts by weight or less, 0.2 parts by weight or less, and particularly preferably 0.1 parts by weight or less, relative to 100 parts by weight of the water-absorbing resin, and the lower limit is in the range of 0.001 parts by weight or more, and preferably 0.01 parts by weight or more.

If the amount of the polyvalent cationic polymer is smaller than 0.001 parts by weight relative to 100 parts by weight of the water-absorbing resin, the FSC does not increase sufficiently, and if the amount is more than 0.5 parts by weight, there is a possibility that the AAP or VDAUP may be decreased to the extent that the present invention is not satisfied, as a result of mixing.

(c) Water-Insoluble Fine Particles

In the fourth production method of the present invention, the water-absorbing resin having particular CRC and AAP values is mixed with a small amount of water-insoluble fine particles. It was found that the water-insoluble fine particles exist on the surface of the particles of the water-absorbing resin having particular CRC and AAP, and act as a steric spacer between the particles, thereby increasing the FSC and VDAUP of the water-absorbing agent.

The water-insoluble fine particles are not particularly limited as long as the fine particles can suppress close adhesion between the particles of the water-absorbing agent when the water-absorbing agent is brought into contact with an aqueous liquid, and allow smooth flow of the aqueous liquid. Examples of organic fine particles include metal soaps, but among others, a water-insoluble inorganic fine powder is preferred. Particularly, the water-insoluble fine particles are preferably inorganic fine particles, and inorganic fine particles of bentonite, silicon dioxide, titanium oxide, aluminum oxide and the like, particularly silicon-type fine particles, are preferred because they increase the free swell capacity without load (FSC). Furthermore, the water-insoluble fine particles may be hydrophilic or may be hydrophobic, but preferably, hydrophilic fine particles exhibiting water-dispersibility can be used. Examples of hydrophilic fine particles, particularly silicon-type fine particles, are disclosed in, for example, EP 0629411.

Furthermore, regarding the water-insoluble fine particles, fine particles having a volume average particle size of 10 μm or less, 5 μm or less, 1 μm or less, and particularly 0.5 μm or less, are preferably used.

The method for mixing the water-absorbing resin and the water-insoluble fine particles may be dry blending, or may be mixing in the form of slurry by preparing an aqueous dispersion liquid of the water-insoluble fine particles. However, dry blending is preferably performed, and the mixing machine at that time is appropriately selected.

The proportion of the water-absorbing resin and the water-insoluble fine particles may be to such an extent that the absorption against pressure (AAP) or the VDAUP is not extremely decreased by the addition of the water-insoluble fine particles, and particularly the decrease of AAP is 5.0 [g/g] or less. The amount of the water-insoluble fine particles may be appropriately determined, but is preferably 0.4 parts by weight or less, 0.3 parts by weight or less, 0.2 parts by weight or less, and particularly preferably 0.1 parts by weight or less, relative to 100 parts by weight of the water-absorbing resin, and the lower limit is in the range of 0.001 parts by weight or more, and preferably 0.01 parts by weight or more.

If the amount of the water-insoluble fine particles is smaller than 0.001 parts by weight relative to 100 parts by weight of the water-absorbing resin, there is no sufficient increase in the FSC, and if the amount is greater than 0.4 parts by weight, there is a possibility that the AAP or VDAUP may be decreased by the mixing to the extent that the present invention is not satisfied.

As discussed above, the water-absorbing agent of the present invention may be obtained by taking the first to fourth production methods of the present invention as examples, but other water-absorbing agents may also be obtained by these production methods, or the water-absorbing agent of the present invention may be obtained by other production methods.

In the production methods described above, a long-chain alkylamine (particularly having 10 to 20 carbon atoms) may be used instead of the polyvalent metal cation, polyvalent cationic polymer, or water-insoluble fine particles.

(α-Hydroxycarboxylic Acid)

In the present invention, in order to enhance the intended physical properties, in order to prevent coloration of the resulting water-absorbing agent, and in order to obtain fixability to pulp at the time of production of diapers, it is preferable that a polycation selected from a polyvalent metal cation and a polyamine polymer is incorporated as an aqueous solution containing a polyhydric alcohol or a hydroxycarboxylic acid in step (B) or after step (B).

The polyhydric alcohol to be used is preferably a non-polymeric water-soluble polyhydric alcohol, and is a polyhydric alcohol exemplified in connection with the surface crosslinking step, particularly propanediol. In the present invention, there is provided a particulate water-absorbing agent which contains or uses in the production step, a polyhydric alcohol in an amount of preferably 0.01 parts to 3 parts by weight, and more preferably 0.02 parts to 2 parts by weight, relative to 100 parts by weight of the water-absorbing resin, and an α-hydroxycarboxylic acid in an amount of preferably 0.01 parts to 3 parts by weight, and more preferably 0.05 parts to 2 parts by weight, relative to 100 parts by weight of the water-absorbing resin.

The α-hydroxycarboxylic acid that is preferably used in the present invention refers to a carboxylic acid in which a hydroxyl group is bonded to the carbon atom at the α-position in the molecule, and is preferably an aliphatic hydroxycarboxylic acid such as a non-polymeric α-hydroxycarboxylic acid, and more preferably an aliphatic α-hydroxycarboxylic acid which does not have a cyclic structure or an unsaturated group. In the case of an aromatic α-hydroxycarboxylic acid or an α-hydroxycarboxylic acid having a cyclic structure or an unsaturated group, the hydroxycarboxylic acid itself is colored by an oxidation reaction, and therefore, it is not preferable. Furthermore, the molecular weight of the compound is preferably in the range of 40 to 2,000, more preferably 60 to 1,000, and particularly preferably 100 to 500. Furthermore, the α-hydroxycarboxylic acid used in the present invention is preferably water-soluble such that the solubility in 100 g of deionized water at 20±5° C. is 1 g or more, more preferably g or more, still more preferably 10 g or more, and particularly preferably 20 g or more. Examples of such an α-hydroxycarboxylic acid include lactic acid (salts), citric acid (salts), malic acid (salts), isocitric acid (salts), glyceric acid (salts), tartaric acid (salts), and D-forms, L-forms and mesoforms thereof. The most preferred examples of a polyvalent α-hydroxycarboxylic acid that may be used include malic acid (salts), citric acid (salts), isocitric acid (salts), and tartaric acid (salts), from the viewpoints of the water absorption characteristics or improvement of coloration.

(2-7) Chelating Agent Addition Step

The particulate water-absorbing agent related to the present invention preferably further contains a chelating agent. By incorporating a chelating agent, a particulate water-absorbing agent having excellent resistance to urine and excellent coloration preventing capability is obtained.

The method for obtaining the particulate water-absorbing agent containing a chelating agent is not particularly limited, and a chelating agent may be appropriately added in the various steps described above. However, various methods such as, for example, a method of adding a chelating agent in advance to an aqueous monomer solution in the polymerization step, a method of adding a chelating agent in the gel fine granulation step, a method of adding a chelating agent before and after the drying step, a method of incorporating a chelating agent in advance to the aqueous solution of a surface crosslinking agent in the surface crosslinking step, or a method of adding a chelating agent separately from the aqueous solution of a surface crosslinking agent, and a method of adding a chelating agent to a water-absorbing resin after surface crosslinking, can be appropriately selected. Furthermore, there are no particular limitations on the form used when the chelating agent is added, and for example, a chelating agent in a liquid form or a solid (powder) form may be added directly, or the chelating agent may be dissolved in advance in a solvent and added as a solution. However, from the viewpoint of handleability or the deviation of the amount of addition, it is preferable to add the chelating agent as a solution.

The chelating agent is not particularly limited, and for example, polymeric or non-polymeric chelating agents may be used. Among them, a non-polymeric chelating agent is preferred, and it is more preferable to use a non-polymeric chelating agent having a molecular weight or weight average molecular weight of preferably 40 to 2,000, more preferably 60 to 1,000, and still more preferably 100 to 500, as a monomer or a polymer thereof. More specific examples of the chelating agent include aminocarboxylic acids (salts) such as trisodium diethylenetriamine pentaacetate, and the number of carboxyl group therein is preferably 2 to 20, more preferably 4 to 10, and particularly preferably 5 to 8.

The using amount of the chelating agent in the present invention is preferably 0.00001 parts to 10 parts by weight, more preferably 0.0001 parts to 1 part by weight, and still more preferably 0.002 parts to 0.1 parts by weight, relative to 100 parts by weight of the water-absorbing resin. If the using amount exceeds 10 parts by weight, effects adequate for the using amount may not be obtained, and problems such as economical inefficiency as well as deterioration of water absorption characteristics occur. On the other hand, if the using amount is less than 0.00001 parts by weight, sufficient effects of addition are not obtained.

(2-8) Deodorant Component Addition Step

In the particulate water-absorbing agent related to the present invention, a deodorant component, preferably a plant component, can be further incorporated in order to impart deodorizing properties. By incorporating a plant component, a particulate water-absorbing agent having excellent deodorizing properties may be obtained.

There are no particular limitations on the plant component, but examples thereof include compounds including polyphenol, flavones, caffeine, tannin, tannic acid, nutgall, gallnut, gallic acid and the like; plants of the Theaceae family, such as camellia, Hikasaki plant and sprague; plants of the Gramineae family, such as rice, sasa-bamboo, bamboo, corn, wheat and barley; and plants of the Rubiaceae family, such as coffee. There are no particular limitations on the form of these plant components, and examples include extracts (essential oils) extracted from plants, plants themselves, and plant residues and extraction residues produced as side products in the production processes in plant processing industry or food processing industry.

The using amount of the plant components in the present invention is larger than 0 parts and less than or equal to 10 parts by weight, preferably 0.001 parts to 5 parts by weight, and more preferably 0.002 parts to 3 parts by weight, relative to 100 parts by weight of the water-absorbing resin. When the using amount is adjusted to the range described above, the plant components exhibit deodorizing properties.

(2-9) Granulation Step

On the present invention, it is preferable to granulate the water-absorbing resin. The amount of water used at the time of granulating the resin may vary depending on the moisture content ratio of the water-absorbing resin, but usually, the amount is preferably 0.5 parts to 20 parts by weight, and more preferably 0.5 parts to 10 parts by weight, relative to 100 parts by weight of the solids content of the water-absorbing resin. Furthermore, a hydrophilic organic solvent may also be used in addition to water. Meanwhile, water, or water and a hydrophilic solvent may be collectively referred to as aqueous liquids.

[3] Physical Properties of Particulate Water-Absorbing Agent

While taking the method for producing a particulate water-absorbing agent described above as an example, the present invention provides a novel particulate water-absorbing agent, that is, a particulate water-absorbing agent containing a polyacrylic acid (salt)-type water-absorbing resin that has been surface-crosslinked as a main component, and containing at least one spacer selected from polycations and water-insoluble fine particles, in which the (a) free swell capacity (FSC) satisfies 55 to 65 [g/g], the (b) absorption against pressure (AAP—4.83 kPa) satisfies 20 to 30 [g/g], and the (c) vertical diffusion absorption amount under pressure (VDAUP) satisfies 30 to 80 g.

The particulate water-absorbing agent related to the present invention is a water-absorbing agent exhibiting unprecedented performance, which is well-balanced between the free swell capacity (FSC), the absorption against pressure (AAP—4.83 kPa), and the vertical diffusion absorption amount under pressure (VDAUP). When the water-absorbing agent is used in an absorbing article (particularly a disposable diaper), the water-absorbing agent can rapidly absorb a large amount of an aqueous liquid all at once, and retain and diffuse the aqueous liquid, the aqueous liquid thus absorbed does not flow back.

The particulate water-absorbing agent related to the present invention contains the spacer described above, preferably at least one spacer selected from a polyvalent metal cation, a polyamine polymer and water-insoluble fine particles, but the spacer is localized at the surface of the particulate water-absorbing agent. This spacer that is present at the surface of the particulate water-absorbing agent causes the free swell capacity (FSC) to increase as compared with the centrifuge retention capacity (CRC), and as a result, the absolute absorption amount in an absorbing article (particularly a disposable diaper) is maximized. It is generally known that the absorption capacities under no added pressure (CRC and FSC) of a water-absorbing resin are correlated with each other (for example, FSC=1.02×CRC+11.32; Non-Patent Literature 1, page 152); however, it was found in the present invention that the FSC increases as compared with the conventional relationship formula. Meanwhile, in the water-absorbing agent of the present invention containing at least one spacer selected from polycations and water-insoluble fine particles, when a polycation is used, the counter anion species in the water-absorbing agent is not particularly limited. For example, the counter anion of the polyvalent metal cation or the polycationic polymer may be an anionic functional group of the water-absorbing resin, particularly a carboxyanion in the case of a polyacrylic acid-type water-absorbing resin, or may be present in the water-absorbing agent in the form of a counter anion of the polyvalent metal salt or the cationic polymer used. That is, in other words, the polycation may have all reacted with the anionic functional groups of the water-absorbing resin, may have partially reacted, or may be included in the water-absorbing agent in its original form.

(3-1) Free Swell Capacity (FSC)

The free swell capacity (FSC) of the particulate water-absorbing agent according to the present invention is 55 to 65 [g/g], preferably 55 to 63 [g/g], more preferably 56 to 63 [g/g], and still more preferably 57 to 63 [g/g]. If the free swell capacity (FSC) is less than 55 [g/g], in the case of using the particulate water-absorbing agent in an absorbing article (particularly a disposable diaper), an excellent absolute absorption amount may not be obtained, which is not preferable.

(3-2) Absorption Against Pressure (AAP—4.83 kPa)

The absorption against pressure (AAP—4.83 kPa) of the particulate water-absorbing agent according to the present invention is 20 to 30 [g/g], preferably 21 to 30 [g/g], more preferably 22 to 30 [g/g], and still more preferably 23 to 30 [g/g]. If the absorption against pressure (AAP—4.83 kPa) is less than 20 [g/g], in the case of using the particulate water-absorbing agent in an absorbing article (particularly a disposable diaper), the re-wet amount (re-wet) increases, which is not preferable.

(3-3) Vertical Diffusion Absorption Amount Under Pressure (VDAUP)

The vertical diffusion absorption amount under pressure (VDAUP) of the particulate water-absorbing agent according to the present invention is 30 to 80 g, preferably 35 to 75 g, more preferably 35 to 70 g, and still more preferably 35 to 65 g. If the vertical diffusion absorption amount under pressure (VDAUP) is less than 30 g, in the case of using the particulate water-absorbing agent in an absorbing article (particularly a disposable diaper), the re-wet amount (re-wet) increases, which is not preferable.

(3-4) Centrifuge Retention Capacity (CRC)

The centrifuge retention capacity (CRC) of the particulate water-absorbing agent according to the present invention is preferably 32 [g/g] or greater, more preferably 33 [g/g] or greater, and still more preferably 34 [g/g] or greater. If the centrifuge retention capacity (CRC) is less than 32 [g/g], there is a risk that when the particulate water-absorbing agent is used in an absorbing article such as a disposable diaper, the particulate water-absorbing agent may not exhibit superior physical properties. Meanwhile, a higher upper limit of the centrifuge retention capacity (CRC) is more preferable, but from the viewpoints of the balance with other physical properties and the production cost, it is usually sufficient if the upper limit is about 45 [g/g], more suitably 40 [g/g], and particularly 38 [g/g].

(3-5) Physiological Saline Flow Conductivity (SFC)

The physiological saline flow conductivity (SFC) of the particulate water-absorbing agent according to the present invention is preferably 30 [$\times 10^{-7}$ s·cm$^3$·g$^{-1}$] or less, more preferably 25 [$\times 10^{-7}$ s·cm$^3$·g$^{-1}$] or less, and still more preferably 20 [$\times 10^{-7}$ s·cm$^3$·g$^{-1}$] or less. Furthermore, from the viewpoints of the balance with other physical properties and the production cost, the lower limit is preferably 1

[×10$^{-7}$ s·cm$^3$·g$^{-1}$] or greater, and more preferably 5 [×10$^7$ s·cm$^3$·g$^{-1}$] or greater. When the physiological saline flow conductivity (SFC) is adjusted to the range described above, in the case of using the particulate water-absorbing agent in an absorbing article (particularly paper diaper), the liquid absorption time, the re-wet amount, and the absolute absorption amount are excellent, which is preferable.

(3-6) Other Physical Properties

The absorption against pressure (AAP—2.06 kPa) of the particulate water-absorbing agent according to the present invention is preferably 20 [g/g] or greater, and more preferably 25 [g/g] or greater. If the absorption against pressure (AAP—2.06 kPa) is less than 20 [g/g], there is a risk that the effects of the present invention may not be exhibited. Meanwhile, a higher upper limit of the absorption against pressure (AAP—2.06 kPa) is more preferable, but from the viewpoints of the balance with other physical properties and the production cost, it is sufficient if the upper limit is about 40 [g/g], and particularly 35 [g/g].

Furthermore, the moisture content ratio (ERT430.2-02) of the particulate water-absorbing agent related to the present invention is appropriately determined on the basis of the moisture content ratio of the water-absorbing resin obtainable after surface crosslinking, the type or amount of the spacer, and the like, but the moisture content ratio is preferably in the range of 0% to 15% by weight, more preferably 0.5% to 10% by weight, and still more preferably 0.6% to 3% by weight. When the spacer and the water-absorbing resin are mixed, in the case of adding the mixture in the form of an aqueous solution, drying may be carried out. However, in the case of adding the mixture in the form of a powder, drying is optional. Accordingly, it is possible to maintain the moisture content ratio high, and also possible to lower the moisture content ratio. These moisture content ratios may be appropriately controlled in accordance with the purpose.

The shape of the particulate water-absorbing agent related to the present invention is not limited to a particular shape as long as the water-absorbing agent is in a particulate form, and examples of the shape include a spherical shape, an approximate spherical shape, an irregular crushed shape (which is a pulverization product), a rod shape, a polyhedral shape, a sausage shape (for example, U.S. Pat. No. 4,973,632), and a particle having creases (for example, U.S. Pat. No. 5,744,564). These particles may be primary particles (single particles), may be granulated particles, or may be mixtures. Furthermore, the particles may also be foamed porous materials. Among these, primary particles or granulated particles having an irregular crushed shape are preferred. Meanwhile, the particle size (mass median particle size (D50), logarithmic standard deviation (σζ), and weight percentage of particles having a particle size of 850 μm or greater or less than 150 μm) and the bulk specific gravity of the particulate water-absorbing agent of the present invention are preferably in the ranges described above.

[4] Use and the Like of Particulate Water-Absorbing Agent

The use of the particulate water-absorbing agent related to the present invention is not particularly limited, but it is preferable that the particulate water-absorbing agent be molded into an absorbent core and used in an absorbing article (for example, paper diaper) as a final consumption product.

(4-1) Absorber

An embodiment of the present invention includes an absorbent core which contains the particulate water-absorbing agent described above. Furthermore, the absorbent core is molded to include a particulate water-absorbing agent, and optionally a fibrous base material, and preferably has a content of the particulate water-absorbing agent of 40% to 90% by weight.

The absorbent core according to the present invention is obtained by molding a particulate water-absorbing agent into a sheet form, a web form, a cylinder form or the like. Meanwhile, the term "absorber" refers to a water-absorbing material obtained by molding a particulate water-absorbing agent and a hydrophilic fiber such as pulp as main components.

The content of the particulate water-absorbing agent in the absorbent core, that is, the weight of the particulate water-absorbing agent relative to the total weight of the particulate water-absorbing agent and the hydrophilic fiber (fibrous base material) (hereinafter, referred to as "core concentration"), is such that as disclosed in Examples (Table 4), if the content of the particulate water-absorbing agent is 40% by weight or greater, the absorbent core exhibits superior effects, particularly a short liquid absorption time, a small re-wet amount (re-wet), and a large absolute absorption amount. That is, the core concentration in the absorbent core of the present invention is preferably 40% to 100% by weight, more preferably 40% to 90% by weight, still more preferably 40% to 80% by weight, and most preferably 50% to 70% by weight, in which range the maximum effects are exhibited.

Furthermore, since the particulate water-absorbing agent of the present invention has satisfactory liquid permeability (physiological saline flow conductivity; SFC), the content of the hydrophilic fiber can be reduced when the particulate water-absorbing agent is used in the absorbent core. Therefore, even if the core concentration is 40% by weight or greater, the liquid diffusibility is satisfactory, and a large amount of an aqueous liquid can be rapidly absorbed and diffused all at once. Furthermore, the water absorption characteristics can be maintained for a long time, and there is no re-wetting of the absorbed aqueous liquid. As discussed above, by using the particulate water-absorbing agent of the present invention, thickness decrease of the absorbent core (particularly a disposable diaper) can be promoted.

(4-2) Absorbing Article

Another embodiment of the present invention includes an absorbing article containing the absorbent core described above.

The absorbing article according to the present invention is a final consumption product intended for water absorption, gelation, moisture retention, water stopping, moisture absorption, and the like. The final consumption material is an absorbing article including the absorbent core described above, a front surface sheet having liquid permeability, and a back surface sheet having liquid impermeability. Specific examples of the absorbing article include a disposable diaper, an incontinence pad, and a sanitary napkin, and a particularly preferred example is a disposable diaper. Meanwhile, the absorbing article can also be applied to other sanitary materials.

Furthermore, the absorbing article (particularly an article for urine absorption, such as a disposable diaper) of the present invention can rapidly absorb and diffuse a large amount of an aqueous liquid all at once, can maintain the water absorption characteristics for a longer time, and does not exhibit re-wetting of the absorbed aqueous liquid. Since the re-wet amount is small, and the dry sensation is satisfactory, the burden of the person who is wearing the article or the care giver is also reduced.

[5] Effects as Absorber and Absorbing Article (5-1) Balance Between Absolute Absorption Amount and Re-Wet Amount (Re-Wet) of Absorber The absorbent core produced by using the particulate water-absorbing agent related to the present invention can achieve a balance between the "absolute absorption amount" and the "re-wet amount (re-wet)", which are contradictory physical properties. That is, the absorbent core of the present invention is an absorbent core having an absolute absorption amount as defined in section (6-13)(2-a) (mini-absorber) of 300 g or greater, and having a re-wet amount as defined in section (6-13) (2-b) (mini absorber) of 0 g to 2.0 g.

The absolute absorption amount (mini absorber) in the absorbent core of the present invention is preferably 300 g or greater, more preferably 310 g or greater, still more preferably 320 g or greater, and particularly preferably 330 g or greater. If the absolute absorption amount (mini absorber) is 300 g or greater, the absolute absorption amount in an actual paper diaper is also excellent. Furthermore, when a user wears the disposable diaper, the sense of wear is satisfactory, and liquid leakage or the occurrence of skin eruption can be suppressed. Meanwhile, a higher upper limit of the absolute absorption amount (mini absorber) is more preferable, but in view of the balance with other physical properties, it is sufficient if the upper limit is about 400 g.

The re-wet amount (re-set) (mini absorber) in the absorbent core of the present invention is preferably 0 g to 2.0 g, more preferably 0 g to 1.5 g, and still more preferably 0 g to 1.0 g. If the re-wet amount is 2 g or less, the amount of re-wetting (re-wet) in an actual paper diaper is also excellent. Furthermore, when a user wears the disposable diaper, the sense of wear is satisfactory, and liquid leakage or the occurrence of skin eruption can be suppressed.

(5-2) Balance Between Liquid Absorption Time, Re-Wet Amount (Re-Wet), and Absolute Absorption Amount of Absorbing Article An absorbing article produced by using the particulate water-absorbing agent related to the present invention is well-balanced between the "absolute absorption amount" and the "re-wet amount (re-wet)", which are contradictory physical properties, and also has excellent "liquid absorption time".

That is, the absorbing article of the present invention satisfies the condition that when the core concentration is 40% by weight, "the liquid absorption time defined in section (6-13) (2-d) is 120 seconds or less, the re-wet amount (re-wet) defined in section (6-13) (2-d) is 25 g or less, and the absolute absorption amount defined in section (6-13) (2-c) is 750 g or greater"; when the core concentration is 50% by weight, the absorbing article satisfies the condition that "the liquid absorption time is 280 seconds (preferably 250 seconds) or less, the re-wet amount (re-wet) is 20 g (preferably 15 g) or less, and the absolute absorption amount is 715 g (preferably 730 g) or greater"; when the core concentration is 60% by weight, the absorbing article satisfies the condition that "the liquid absorption time is 400 seconds (preferably 300 seconds) or less, the re-wet amount (re-wet) is 15 g (preferably 13 g) or less, and the absolute absorption amount is 700 g (preferably 715 g) or greater"; and when the core concentration is 70% by weight, "the liquid absorption time is 700 seconds (preferably 600 seconds) or less, the re-wet amount (re-wet) is 16 g (preferably 13 g) or less, and the absolute absorption amount is 690 g (preferably 700 g) or greater. Therefore, an absorbing article which uses the particulate water-absorbing agent of the present invention in an amount of 40% to 100% by weight can achieve a balance between the liquid absorption time and the re-wet amount (re-wet) in a broad range, and therefore, the absolute absorption amount in an actual diaper is also excellent. Furthermore, when a user wears the disposable diaper, the sense of wear is satisfactory, and liquid leakage or the occurrence of skin eruption can be suppressed.

Meanwhile, the present application is based on JP 2010-222533 A filed Sep. 30, 2010, and JP 2011-118003 A filed May 26, 2011, the entire disclosures of which are incorporated herein by reference.

EXAMPLES

[6] Examples

Hereinafter, the present invention will be more specifically explained by way of Examples and Comparative Examples. Meanwhile, the electrical devices and the like used in Examples and Comparative Examples were all used under the conditions of 100 V and 60 Hz. Furthermore, unless stated otherwise, various physical properties were measured under the conditions of room temperature (25° C.±2° C.) and a relative humidity of 50% RH.

Furthermore, for convenience, the unit "% by weight" may be indicated as "wt %", and "liter" as "L". Also, in the present specification, the "0.90% by weight of aqueous solution of sodium chloride" may be referred to as "physiological saline", but both will be considered the same. Furthermore, in the following sections (6-1) to (6-13), what is indicated as "particulate water-absorbing agent" for convenience will be replaced by "water-absorbing resin particles" or "water-absorbing resin", when the physical properties of the relevant terms are measured.

(6-1) Centrifuge Retention Capacity (CRC)

The centrifuge retention capacity (CRC) of the particulate water-absorbing agent related to the present invention was measured according to ERT441.2-02.

That is, 0.200 g (weight W0 [g]) of a particulate water-absorbing agent was weighed, and was uniformly inserted into a pouch made of a non-woven fabric (60×85 mm) and heat-sealed. Subsequently, the pouch was immersed in 500 mL of 0.90% by weight of aqueous solution of sodium chloride that had been temperature-regulated at 25±3° C. After 30 minutes had passed, the pouch was pulled out, and dehydration was carried out by using a centrifuge (centrifuge manufactured by Kokusan Corp.; Model H-122) under the conditions of 250 G for 3 minutes. Thereafter, the weight of the pouch (W1 [g]) was measured.

The same operation was carried out without inserting the particulate water-absorbing agent, and the weight of the pouch at that time (W2 [g]) was measured. The centrifuge retention capacity (CRC) was calculated from W0 [g], W1 [g], and W2 [g] thus obtained, according to the following formula.

$$CRC\ [g/g] = \{(W1-W2)/W0\} - 1 \text{[Mathematical formula 2]}$$

(6-2) Free Swell Capacity (FSC)

The free swell capacity (FSC) of the particulate water-absorbing agent related to the present invention was measured according to ERT440.2-02.

That is, 0.200 g (weight W3 [g]) of a particulate water-absorbing agent was weighed, and was uniformly inserted into a pouch (60×85 mm) made of a non-woven fabric and heat-sealed. Subsequently, the pouch was immersed in 500 mL of a 0.90% by weight of aqueous solution of sodium chloride that had been temperature-regulated to 25±3° C. After 30 minutes had passed, the pouch was pulled out, and dehydration was carried out by suspending the pouch for 10 minutes. Thereafter, the weight of the pouch (W4 [g]) was measured.

The same operation was carried out without inserting the particulate water-absorbing agent, and the weight of the pouch at that time (W5 [g]) was measured. The free swell capacity (FSC) was calculated from W3 [g], W4 [g], and W5 [g] thus obtained, according to the following formula.

$$FSC\ [g/g] = \{(W4 - W5)/W3\}1 \quad \text{[Mathematical formula 3]}$$

(6-3) Absorption Against Pressure (AAP)

The absorption against pressure (AAP) of the particulate water-absorbing agent related to the present invention was measured according to ERT442.2-02.

That is, 0.9 g (weight W6 [g]) of a particulate water-absorbing agent was introduced into a measurement apparatus, and the weight of the full set of the measurement apparatus (W7 [g]) was measured. Subsequently, a 0.90% by weight of aqueous solution of sodium chloride was absorbed under a load of 2.06 kPa (0.3 psi, 21 [g/cm$^2$]) or 4.83 kPa (0.7 psi, 50 [g/cm$^2$]). After one hour had passed, the weight of the full set of the measurement apparatus (W8 [g]) was measured, and the absorption against pressure (AAP) was calculated from W6 [g], W7 [g], and W8 [g] thus obtained, according to the following formula (for the apparatus, see FIG. 1). Meanwhile, the measurement apparatus as illustrated in FIG. 1 is an apparatus including a plastic supporting cylinder 100, a stainless steel 400-mesh wire screen 101, a piston 103, and a load (weight) 104, and W8 is the weight including the weight of a water-absorbing agent (swollen gel) 102.

$$AAP\ [g/g] = (W8 - W7)/W6 \quad \text{[Mathematical formula 4]}$$

Meanwhile, the absorption against pressure measured at 2.06 kPa is indicated as "AAP—2.06 kPa", and the absorption against pressure measured at 4.83 kPa is indicated as "AAP—4.83 kPa".

(6-4) Vertical Diffusion Absorption Amount Under Pressure (VDAUP)

The vertical diffusion absorption amount under pressure (VDAUP) of the particulate water-absorbing agent related to the present invention was measured by the same technique as that used in the measurement of the absorption against pressure (AAP) in section (5-3), except that the using amount of the particulate water-absorbing agent was set to 10.000±0.050 g, and the load condition was set to 4.83 kPa (0.7 psi, 50 [g/cm]).

That is, 10.000±0.050 g of a particulate water-absorbing agent was introduced into a measurement apparatus, and the weight of the full set of the measurement apparatus (W9 [g]) was measured. Subsequently, a 0.90% by weight of aqueous solution of sodium chloride was absorbed under a load of 4.83 kPa (0.7 psi, 50 [g/cm$^2$]). After one hour had passed, the weight of the full-set of the measurement apparatus (W10 [g]) was measured, and the vertical diffusion absorption amount under pressure (VDAUP) was calculated from W9 [g] and W10 [g] thus obtained, according to the following formula.

$$VDAUP\ [g] = W10 - W9 \quad \text{[Mathematical formula 5]}$$

(6-5) Physiological Saline Flow Conductivity (SFC)

The SFC is a well-known measurement method, and the measurement was carried out by the technique described in U.S. Pat. No. 5,562,646.

(6-6) Water-Extractable (Ext)

The water-extractable (Ext) of the particulate water-absorbing agent related to the present invention was measured according to ERT470.2-02.

That is, in a plastic container with a lid having a capacity of 250 mL, in which a rotor having a length of 35 mm was introduced, 1.0 g of a particulate water-absorbing agent and 200.0 g of a 0.90% by weight of aqueous solution of sodium chloride were introduced, and the mixture as stirred for 16 hours in an atmosphere at 20° C. to 25° C. (room temperature) and a relative humidity of 50±5 RH %. Thus, a water-extractable in the particulate water-absorbing agent was extracted. Subsequently, the relevant extract was filtered by using one sheet of filter paper (Advantec Toyo Kaisha, Ltd., product name: JIS P 3801, No. 2, thickness: 0.26 mm, retained particle size: 5 μm), and 50.0 g of the filtrate thus obtained was used as a solution for measurement. Next, the solution for measurement was titrated with a 0.1 N aqueous NaOH solution until the pH value reached 10, and then the solution for measurement was titrated with a 0.1 N aqueous HCl solution until the pH value reached 2.7. The amounts of titration at this time ([NaOH] mL and [HCl] mL) were determined.

The same operation was carried out only with the 0.90% by weight of aqueous solution of sodium chloride, and the amounts of blank titration ([bNaOH] mL and [bHCl] mL) were determined.

In the case of the particulate water-absorbing agent of the present invention, the water-extractable (Ext) was calculated according to the following formula, based on the average molecular weight of the monomers used and the amount of titration obtained from the operation described above.

$$Ext\ [\%\ by\ weight] = 0.1 \times (\text{Average molecular weight of monomers}) \times 200.0 \times 100 \times \{[HCl] - [bHCl]\} / 1000 / 1.0 / 50.0 \quad \text{[Mathematical formula 6]}$$

Meanwhile, if the average molecular weight of the monomers is unknown, the average molecular weight of the monomers is calculated by using the neutralization ratio determined by the titration operation described above. The neutralization ratio was determined according to the following formula.

$$\text{Neutralization ratio [mol \%]} = \{1 - ([NaOH] - [bNaOH]) / ([HCl] - [bHCl])\} \times 100 \quad \text{[Mathematical formula 7]}$$

(6-7) pH

The pH of the particulate water-absorbing agent related to the present invention was measured according to ERT400.2-02.

That is, in a beaker having a capacity of 250 mL, 100 mL of a 0.90% by weight of aqueous solution of sodium chloride was placed, and the aqueous solution was slowly stirred (for example, the speed of rotation was 100 rpm) with a magnetic stirrer (length: 30 mm, external diameter: 6 mm) in an atmosphere at 20° C. to 25° C. (room temperature) and a relative humidity of 50±5 RH %. In this state, 0.5 g of a particulate water-absorbing agent was introduced therein, and stirring was continued in the same condition. After 10 minutes had passed, rotation of the magnetic stirrer was stopped, and the mixture was left to stand. After one minute had passed, a pH electrode was immersed in the supernatant portion, and pH measurement was carried out. Meanwhile, regarding the pH electrode, an electrode corrected with standard solutions at pH 4.0 and pH 7.0 was used.

(6-8) Moisture Content Ratio

The moisture content ratio of the particulate water-absorbing agent related to the present invention was measured according to ERT430.2-02.

That is, in an aluminum cup having a bottom surface with a diameter of about 50 mm, 1.00 g of a particulate water-absorbing agent was weighed, and the total weight W11 [g] of the sample (particulate water-absorbing agent and aluminum cup) was measured.

Next, the sample was left to stand in an airless oven at an atmosphere temperature of 105° C., and the particulate water-absorbing agent was dried. After 3 hours had passed, the sample was taken out from the oven, and was cooled to room temperature in a desiccator. Thereafter, the total weight W12 [g] of the sample obtained after drying (particulate water-absorbing agent after drying and aluminum cup) was measured, and the moisture content ratio [% by weight] was calculated according to the following formula.

Moisture content ratio [% by weight]= $(W11-W12)/$(weight of particulate water absorbent)$\times 100$ [Mathematical formula 8]

Meanwhile, when it is necessary to perform solids content compensation for the physical properties of the particulate water-absorbing agent, the moisture content ratio (solids content) was determined by changing the drying temperature to 180° C. The relation between the moisture content ratio and the solids content is as illustrated by the following formula.

Solids content [% by weight]=100−(Moisture content ratio) [Mathematical formula 9]

(6-9) Mass Median Particle Size (D50), Logarithmic Standard Deviation ($\sigma\zeta$) of Particle Size Distribution, and Weight Percentage of Particles Having Particle Size of Less than 150 μm (Particle Content Ratio)

The mass median particle size (D50), the logarithmic standard deviation ($\sigma\zeta$) of the particle size distribution, and the weight percentage of particles having a particle size of less than 150 μm (particle content ratio) of the particulate water-absorbing agent related to the present invention were measured according to the measurement methods disclosed in EP 0349240.

That is, 10.00 g of a particulate water-absorbing agent was classified by using JIS standard sieves (the IIDA Testing Sieve: internal diameter 80 mm; JIS Z8801-1 (2000)) having mesh sizes of 850 μm, 710 μm, 600 μm, 500 μm, 425 μm, 300 μm, 212 μm, 150 μm, 106 μm, and 75 μm, or sieves equivalent to JIS standard sieves. After classification, the weight of each sieve was measured, and the weight percentage (o by weight) of particles having a particle size of less than 150 μm was calculated. Meanwhile, the term "weight percentage of particles having a particle size of less than 150 μm" means the proportion by weight of particles that pass through the JIS standard sieve having a mesh size of 150 μm relative to the total amount of the particulate water-absorbing agent.

Furthermore, in regard to the mass median particle size (D50), the residual percentages R of various particle sizes were plotted in a logarithmic probability paper, and from this graph, the particle size corresponding to R=50% by weight was read as the mass median particle size (D50). Meanwhile, the mass median particle size (D50) refers to the particle size of a standard sieve corresponding to 50% by weight of the total amount of the particulate water-absorbing agent.

Furthermore, the logarithmic standard deviation ($\sigma\zeta$) of the particle size distribution was calculated according to the following formula. Meanwhile, in regard to the logarithmic standard deviation ($\sigma\zeta$) of the particle size distribution, a smaller value thereof means a narrower particle size distribution.

$\sigma\zeta = 0.5 \times \ln(X2/X1)$ [Mathematical formula 10]

Meanwhile, X1 represents the particle size corresponding to R=84.1% by weight, and X2 represents the particle size corresponding to R=15.9% by weight.

(6-10) Polyvalent Metal Cation in Particulate Water-Absorbing Agent

The polyvalent metal cation in the particulate water-absorbing agent related to the present invention was measured according to the "method for quantitatively determining the polyvalent metal component contained in a water absorbent resin" disclosed in Patent Literature 2 (JP 2005-113117 A).

That is, 1.0 g of a particulate water-absorbing agent was weighed in a polypropylene beaker having a capacity of 260 mL, and 190.0 g of physiological saline (0.90% by weight of aqueous solution of sodium chloride) and 10.0 g of 2 N hydrochloric acid were added thereto. The mixture was stirred for 30 minutes at room temperature. After stirring, the supernatant was filtered with a chromatodisc (GL Chromatodisc 25A, GL Sciences, Inc.), and the filtrate thus obtained was analyzed by using a plasma emission spectrometer (manufactured by Horiba, Ltd., ULTIMA). Thus, the polyvalent metal cation concentration was determined. Meanwhile, the calibration curve was produced by using physiological saline containing known amounts of a polyvalent metal cation. Based on the polyvalent metal cation concentration thus determined, the polyvalent metal cation concentration in the particulate water-absorbing agent is represented by the following formula.

Polyvalent metal cation concentration in particulate water-absorbing agent [% by weight]=(polyvalent metal cation concentration in solution)×200.0 [Mathematical formula 11]

(6-11) Polyamine Polymer in Particulate Water-Absorbing Agent

The polyamine polymer in the particulate water-absorbing agent related to the present invention was measured by the technique described below.

That is, 1.0 g of a particulate water-absorbing agent was weighed in a polypropylene beaker having a capacity of 260 mL, and 200.0 g of 0.1 N hydrochloric acid (liquid temperature: 20° C. to 25° C.) was added thereto. The mixture was stirred for one hour at room temperature, and the polyamine polymer was isolated from the particulate water-absorbing agent. After stirring, the supernatant was filtered with a chromatodisc (GL Chromatodisc 25A, GL Sciences, Inc.), and the filtrate thus obtained was analyzed by using GPC (gel permeation chromatography) to determine the polyamine polymer concentration.

(6-12) Water-Insoluble Fine Particles in Particulate Water-Absorbing Agent

The water-insoluble fine particles in the particulate water-absorbing agent related to the present invention was measured by the technique described below. Meanwhile, a particulate water-absorbing agent containing silicon-type fine particles (silicon dioxide) as water-insoluble fine particles will be described as an example, but in the case of fine particles containing other elements, the amount can be quantitatively determined by appropriately changing the measurement conditions.

That is, 0.500 g of a particulate water-absorbing agent was weighed in a polypropylene beaker having a capacity of 250 mL, and 0.5 g of (anhydrous) sodium carbonate of reagent grade was added thereto. 100 mL of deionized water (grade 3, ISO3696) at 80° C. was further added thereto. While the temperature of the content was maintained at 80° C., the content was stirred for 2 hours, and thus silicon dioxide in the particulate water-absorbing agent was dissolved.

Subsequently, the content was filtered by using a quantitative filter paper (Advantec Toyo Kaisha, Ltd.; No. 5C, 185 mm), and at the time point where there was almost no liquid on the filter paper (about 1 hour), 3 mL of 6 N hydrochloric acid was added to the filtrate so as to cause the swollen particulate water-absorbing agent (gel) to shrink as much as possible.

Subsequently, in a graduated cylinder having a capacity of 200 mL, the filtrate (containing 3 mL of 6 N hydrochloric acid) and 4 mL of a 5% by weight of aqueous solution of ammonium molybdenum were added two times. Deionized water was added there to adjust the volume, and the content was caused to develop color. The absorbance (ABS) of the colored liquid thus obtained was measured within 5 to 20 seconds after coloration by using a spectrophotometer (manufactured by Hitachi, Ltd., IU-1100 Spectrophotometer) at a wavelength of 410 nm and a cell having a thickness of 10 mm. Meanwhile the same operation was carried out by using deionized water as a blank.

For the absorbances obtained by the operation described above, the difference (absorbance of the colored liquid–absorbance of the blank) was taken as the absorbance of the test sample, and the amount of silicon dioxide (% by weight) in the particulate water-absorbing agent was determined by using a calibration curve that will be described below.

Meanwhile, the calibration curve was produced by preparing standard samples by adding 0 parts by weight, 0.03 parts by weight, 0.06 parts by weight, 0.1 parts by weight, 0.2 parts by weight, 0.3 parts by weight, 0.5 parts by weight, and 1.0 part by weight of silicon dioxide fine particles (for example, manufactured by Nippon Aerosil Co., Ltd.; Aerosil (registered trademark) 200), respectively, to 100 parts by weight of a particulate water-absorbing agent that did not contain silicon dioxide (for example, the particulate water-absorbing agent (1) obtained in Example 1) and mixing the samples, subjecting these standard samples to the same operation as described above, and thereby determining the absorbances.

(6-13) Performance Evaluation of Absorber

In regard to the particulate water-absorbing agent related to the present invention, various absorbers (mini absorbers, paper diaper type absorbers) listed below were produced in order to evaluate the performance as absorbers, and the absolute absorption amount, the re-wet amount and the liquid absorption time were measured and evaluated.

(1) Production of Absorber (1-a) Mini Absorber 1

2 g of a particulate water-absorbing agent and 2 g of wood pulverized pulp were dry mixed by using a mixer, and then the mixture thus obtained was spread on a 400-mesh wire screen (mesh size: 38 μm) to form a web having a diameter of 90 mm. Subsequently, the web was pressed for one minute at a pressure of 196.14 kPa (2 [kgf/cm$^2$]), and thereby a mini absorber 1 was obtained.

The content of the particulate water-absorbing agent in the mini absorber 1 thus obtained was about 1.9 g, and the basis weight was about 0.06 [g/cm$^2$].

(1-b) Mini Absorber 2

5 g of a particulate water-absorbing agent and 5 g of wood pulverized pulp were dry mixed by using a mixer, and then the mixture thus obtained was spread on a 400-mesh (mesh size: 38 μm) wire screen to form a web of a rectangular shape (size: 100 mm×167 mm). Subsequently, the web was pressed for one minute at a pressure of 196.14 kPa (2 [kgf/cm$^2$]), and thereby a mini absorber 2 was obtained.

The content of the particulate water-absorbing agent in the mini absorber 2 thus obtained was about 5.0 g, and the basis weight was about 0.06 [g/cm$^2$].

(1-c) Paper Diaper Type Absorber 3

30 g of a particulate water-absorbing agent and 70 g of wood pulverized pulp were dry mixed by using a mixer, and then the mixture thus obtained was spread on a 400-mesh wire screen (mesh size: 38 μm). The mixture was subjected to air papermaking in a web form (sheet form) by using a batch type air papermaking apparatus. Thereafter, the web was shaped by cutting the web into a rectangular shape (size: 120 mm×380 mm). Subsequently, the web was pressed for one minute at a pressure of 196.14 kPa (2 [kgf/cm$^2$]), and thereby a disposable diaper type absorber 3 (size of a disposable diaper for children) was obtained.

The content of the particulate water-absorbing agent in the disposable diaper type absorber 3 thus obtained was 12 g, the core concentration was 30%, and the basis weight was about 877 [g/m$^2$].

(1-d) Paper Diaper Type Absorber 4

40 g of a particulate water-absorbing agent and 60 g of wood pulverized pulp were dry mixed by using a mixer, and then the mixture thus obtained was spread on a 400-mesh wire screen (mesh size: 38 μm). The mixture was subjected to air papermaking in a web form (sheet form) by using a batch type air papermaking apparatus. Meanwhile, the basis weight was adjusted by means of the air papermaking time. Thereafter, the web was shaped by cutting the web into a rectangular shape (size: 120 mm×380 mm). Subsequently, the web was pressed for one minute at a pressure of 196.14 kPa (2 [kgf/cm$^2$]), and thereby a disposable diaper type absorber 4 (size of a disposable diaper for children) was obtained.

The content of the particulate water-absorbing agent in the disposable diaper type absorber 4 thus obtained was 12 g, the core concentration was 40%, and the basis weight was about 658 [g/m$^2$].

(1-e) Paper Diaper Type Absorber 5

50 g of a particulate water-absorbing agent and 50 g of wood pulverized pulp were dry mixed by using a mixer, and then the mixture thus obtained was spread on a 400-mesh wire screen (mesh size: 38 μm). The mixture was subjected to air papermaking in a web form (sheet form) by using a batch type air papermaking apparatus. Meanwhile, the basis weight was adjusted by means of the air papermaking time. Thereafter, the web was shaped by cutting the web into a rectangular shape (size: 120 mm×380 mm). Subsequently, the web was pressed for one minute at a pressure of 196.14 kPa (2 [kgf/cm]), and thereby a disposable diaper type absorber 5 was obtained.

The content of the particulate water-absorbing agent in the disposable diaper type absorber 5 thus obtained was 12 g, the core concentration was 50%, and the basis weight was about 526 [g/m$^2$].

(1-f) Paper Diaper Type Absorber 6

60 g of a particulate water-absorbing agent and 40 g of wood pulverized pulp were dry mixed by using a mixer, and then the mixture thus obtained was spread on a 400-mesh wire screen (mesh size: 38 μm). The mixture was subjected to air papermaking in a web form (sheet form) by using a batch type air papermaking apparatus. Meanwhile, the basis weight was adjusted by means of the air papermaking time. Thereafter, the web was shaped by cutting the web into a rectangular shape (size: 120 mm×380 mm). Subsequently, the web was pressed for one minute at a pressure of 196.14 kPa (2 [kgf/cm]), and thereby a disposable diaper type absorber 6 was obtained.

The content of the particulate water-absorbing agent in the disposable diaper type absorber 6 thus obtained was 12 g, the core concentration was 60%, and the basis weight was about 439 [g/m$^2$].

(1-g) Paper Diaper Type Absorber 7

70 g of a particulate water-absorbing agent and 30 g of wood pulverized pulp were dry mixed by using a mixer, and then the mixture thus obtained was spread on a 400-mesh wire screen (mesh size: 38 µm). The mixture was subjected to air papermaking in a web form (sheet form) by using a batch type air papermaking apparatus. Meanwhile, the basis weight was adjusted by means of the air papermaking time. Thereafter, the web was shaped by cutting the web into a rectangular shape (size: 120 mm×380 mm). Subsequently, the web was pressed for one minute at a pressure of 196.14 kPa (2 [kgf/cm$^2$]), and thereby a disposable diaper type absorber 7 was obtained.

The content of the particulate water-absorbing agent in the disposable diaper type absorber 7 thus obtained was 12 g, the core concentration was 70%, and the basis weight was about 376 [g/m$^2$].

(2) Performance Evaluation (2-a) Absolute Absorption Amount (Mini Absorber)

The mini absorber 2 (size: 100 mm×167 mm; core concentration: 50%) described above was inserted into a pouch (size: 120×180 mm) made of a non-woven fabric and was heat-sealed. Subsequently, the pouch was immersed in 2 L of a 0.90% by weight of aqueous solution of sodium chloride that was temperature-regulated at 25±3° C. After 30 minutes had passed, the pouch was pulled out and suspended for 10 minutes to dehydrate. The weight of the pouch (W13 [g]) was measured.

The same operation was carried out without inserting the mini absorber 2, and the weight of the pouch at that time (W14 [g]) was measured. The absolute absorption amount [g] of the mini absorber was calculated according to the following formula.

Absolute absorption amount (mini absorber) [g]=$W13-W14$     [Mathematical Formula 12]

(2-b) Re-Wet Amount (Re-Wet) (Mini Absorber)

The mini absorber 1 (diameter: 90 mm; core concentration 50%) described above was placed on the bottom of a Petri dish made of SUS and having an internal diameter of 90 mm, and a non-woven fabric having a diameter of 90 mm was mounted thereon. Furthermore, a piston and a weight were placed thereon such that a load of 4.8 kPa would be evenly exerted on the mini absorber 1. Meanwhile, the piston and the weight used each had a liquid feed port with a diameter of 5 mm at the center.

Subsequently, 25 mL of physiological saline (0.90% by weight of aqueous solution of sodium chloride) was allowed to flow in through the liquid feed ports, and was absorbed into the mini absorber 1. After 30 minutes had passed, 25 mL of physiological saline was further allowed to flow in through the liquid feed ports, and was absorbed.

After 30 minutes had passed, the piston and the weight were removed, and 30 sheets of filter paper (manufactured by Toyo Roshi Kaisha, Ltd.; No. 2) having an external diameter of 90 mm, the total weight (W15 [g]) of which had been measured in advance, were mounted thereon. Then, a piston and a weight (total weight: 20 kg) which would evenly exert a load were rapidly mounted thereon.

After 5 minutes had passed, the weight of the 30 sheets of filter paper (W16 [g]) was measured, and the re-wet amount [g] of the mini absorber 1 was calculated according to the following formula.

Re-wet amount (mini absorber) [g]= $W16-W15$     [Mathematical formula 13]

(2-c) Absolute Absorption Amount (Paper Diaper Type Absorber)

The disposable diaper type absorbers 3 to 7 (size: 120 mm×380 mm; core concentration: 30% to 70%) were each inserted into a pouch (size: 130×400 mm) made of a non-woven fabric and was heat-sealed. Subsequently, the pouch was immersed in 5 L of a 0.9% by weight of aqueous solution of sodium chloride that was temperature-regulated at 25±3° C. After 30 minutes had passed, the pouch was pulled out and suspended for 10 minutes to dehydrate. The weight of the pouch (W17 [g]) was measured.

The same operation was carried out without inserting the disposable diaper type absorbers 3 to 7, and the weights of the pouches at that time (W18 [g]) were measured. The absolute absorption amounts [g] of the disposable diaper type absorbers 3 to 7 were calculated according to the following formula.

Absolute absorption amount (paper diaper type absorber) [g]=$W17-W18$     [Mathematical formula 14]

(2-d) Liquid Absorption Time, Re-Wet Amount (Re-Wet) (Paper Diaper Type Absorber)

A pseudo-paper diaper was produced according to the method described below.

That is, on a back sheet (liquid-impermeable sheet) made of liquid-impermeable polypropylene and having a size of 120 mm×380 mm, a disposable diaper type absorber described above (any one of absorbers 3 to 7) was mounted, and a non-woven fabric having a size of 120 mm×380 mm and a top sheet (liquid-permeable sheet) made of liquid-permeable polypropylene and having the same size were further placed hereon. Thus, a pseudo-paper diaper composed of four layers was produced. Subsequently, an acrylic plate (size: 120 mm×380 mm) having a liquid feed port with a diameter of 70 mm at the center was placed on the pseudo-paper diaper. A weight that was adjusted so as to evenly exert a load of 2.1 kPa over the entire surface was further placed thereon.

Subsequently, 75 ml of physiological saline (0.90% by weight of aqueous solution of sodium chloride) was poured through the liquid feed port 5 times in total at an interval of 30 minutes (total feed amount: 375 ml). The time taken by the physiological saline fed for the fifth time to be absorbed into the disposable diaper type absorber (that is, the time taken by physiological saline to be absorbed from the top of the liquid-permeable sheet) was recorded as the "liquid absorption time".

After the measurement of the liquid absorption time, after 30 minutes had passed, the weight and the acrylic plate were removed, and 30 sheets of kitchen towel (size: 120 mm×380 mm, manufactured by Oji Nepia Co., Ltd.), the total weight (W19 [g]) of which had been measured in advance, were mounted thereon. Then, an acrylic plate (size: 120 mm×380 mm) and a weight (total weight: 10 kg) which would evenly exert a load were rapidly placed thereon.

After one minute had passed, the weight of the 30 sheets of kitchen towel (W20 [g]) was measured. Thus, the re-wet amounts [g] of the disposable diaper type absorbers 3 to 7 were calculated according to the following formula.

Re-wet amount (paper diaper type absorber) [g]=$W20-W19$     [Mathematical formula 15]

Production Example 1

In a reactor formed by attaching a lid to a double-blade type jacketed stainless steel kneader having two sigma-shaped blades and having an internal capacity of 10 L, 425.2 g of acrylic acid, 4499.5 g of a 37% by weight of aqueous solution of sodium acrylate, 538.5 g of pure water, 6.17 g of polyethylene glycol diacrylate (molecular weight 523), and 0.21 g of trisodium diethylenetriamine pentaacetate were introduced to prepare a reaction liquid, and then the reaction liquid was degassed for 20 minutes in a nitrogen gas atmosphere.

Subsequently, 28.3 g of a 10% by weight of aqueous solution of sodium persulfate and 23.6 g of a 0.1% by weight of aqueous solution of L-ascorbic acid were separately added to the reaction liquid while the reaction liquid was stirred. Polymerization was initiated after about 25 seconds. Furthermore, while the water-containing gel-like crosslinked polymer thus produced was crushed, polymerization was carried out at 25° C. to 95° C., and after 30 minutes from the initiation of polymerization, the water-containing gel-like crosslinked polymer was removed from the reactor. The water-containing gel-like crosslinked polymer thus obtained was finely granulated to particles having a diameter of about 5 mm or less.

The water-containing gel-like crosslinked polymer thus finely granulated was spread on a wire screen having a mesh size of 300 μm (50-mesh) and was hot air dried at 170° C. for 65 minutes. Subsequently, the finely granulated polymer was pulverized with a roll mill, further classified with a JIS standard sieve having a mesh size of 850 μm, and prepared. Through this series of operations, water-absorbing resin particles (1) of an irregular pulverized shape, having a mass median particle size (D50) of 458 μm and a logarithmic standard deviation ($\sigma\zeta$) of the particle size distribution of 0.40, were obtained. The centrifuge retention capacity (CRC) of the water-absorbing resin particles (1) thus obtained was 42 [g/g], and the water-extractable (Ext) was 13% by weight.

Production Example 2

The same operation as that carried out in Production Example 1 was carried out, except that the using amount of polyethylene glycol diacrylate (molecular weight 523) used in Production Example 1 was changed to 6.78 g. Thus, water-absorbing resin particles (2) of an irregular pulverized shape, having a mass median particle size (D50) of 380 μm and a logarithmic standard deviation ($\sigma\zeta$) of the particle size distribution of 0.35, were obtained. The centrifuge retention capacity (CRC) of the water-absorbing resin particles (2) thus obtained was 39 [g/g], and the water-extractable (Ext) was 11% by weight.

Production Example 3

The same operation as that carried out in Production Example 1 was carried out, except that the using amount of polyethylene glycol diacrylate (molecular weight 523) used in Production Example 1 was changed to 4.93 g. Thus, water-absorbing resin particles (3) of an irregular pulverized shape, having a mass median particle size (D50) of 380 μm and a logarithmic standard deviation ($\sigma\zeta$) of the particle size distribution of 0.33, were obtained. The centrifuge retention capacity (CRC) of the water-absorbing resin particles (3) thus obtained was 45 [g/g], and the water-extractable (Ext) was 15% by weight.

Production Example 4

The same operation as that carried out in Production Example 1 was carried out, except that the using amount of polyethylene glycol diacrylate (molecular weight 523) used in Production Example 1 was changed to 7.39 g. Thus, water-absorbing resin particles (4) of an irregular pulverized shape, having a mass median particle size (D50) of 470 μm and a logarithmic standard deviation ($\sigma\zeta$) of the particle size distribution of 0.42, were obtained. The centrifuge retention capacity (CRC) of the water-absorbing resin particles (4) thus obtained was 36 [g/g], and the water-extractable (Ext) was 9% by weight.

Production Example 5

The same operation as that carried out in Production Example 1 was carried out, except that the using amount of polyethylene glycol diacrylate (molecular weight 523) used in Production Example 1 was changed to 2.46 g. Thus, water-absorbing resin particles (5) of an irregular pulverized shape, having a mass median particle size (D50) of 470 μm and a logarithmic standard deviation ($\sigma\zeta$) of the particle size distribution of 0.42, were obtained. The centrifuge retention capacity (CRC) of the water-absorbing resin particles (5) thus obtained was 55 [g/g], and the water-extractable (Ext) was 20% by weight.

Production Example 6

The same operation as that carried out in Production Example 1 was carried out, except that the using amount of polyethylene glycol diacrylate (molecular weight 523) used in Production Example 1 was changed to 3.08 g. Thus, water-absorbing resin particles (6) of an irregular pulverized shape, having a mass median particle size (D50) of 470 μm and a logarithmic standard deviation ($\sigma\zeta$) of the particle size distribution of 0.42, were obtained. The centrifuge retention capacity (CRC) of the water-absorbing resin particles (6) thus obtained was 53 [g/g], and the water-extractable (Ext) was 17% by weight.

Production Example 7

The same operation as that carried out in Production Example 1 was carried out, except that the using amount of polyethylene glycol diacrylate (molecular weight 523) used in Production Example 1 was changed to 8.60 g. Thus, water-absorbing resin particles (7) of an irregular pulverized shape, having a mass median particle size (D50) of 455 μm and a logarithmic standard deviation ($\sigma\zeta$) of the particle size distribution of 0.41, were obtained. The centrifuge retention capacity (CRC) of the water-absorbing resin particles (7) thus obtained was 33 [g/g], and the water-extractable (Ext) was 8% by weight.

Production Example 8

Production was carried out according to, among the water-absorbing agents described in Examples of Patent Literature 1, Example 23 that exhibited the highest centrifuge retention capacity and the highest absorption against pressure.

That is, a solution (A) prepared by mixing 185.4 g of acrylic acid, 0.942 g of polyethylene glycol diacrylate (molecular weight 523) (0.07 mol % relative to acrylic acid), and 1.13 g of a 1.0% by weight of aqueous solution of pentasodium diethylenetriamine pentaacetate, was introduced into a polypropylene container having an internal diameter of 80 mm and a capacity of 1 L, which was covered with Styrofoam, an insulating material. While the solution was stirred with a magnetic stirrer, a solution (B) prepared by mixing 148.53 g of a 48.5% by weight of aqueous solution of sodium hydroxide and 159.71 g of ion-exchanged water that was temperature-regulated at 50° C., was rapidly added to and mixed with the solution (A) in an open system. Thus, an aqueous monomer solution was obtained. The aqueous monomer solution was such that the temperature of the liquid increased up to about 100° C. due to the heat of neutralization and the heat of dissolution.

Subsequently, 4.29 g of a 3.0% by weight of aqueous solution of sodium persulfate was added to the aqueous monomer solution while being stirred, and then the mixture was immediately poured into a stainless steel vat-type container (bottom surface: 250×250 mm, top surface: 640× 640 mm, height: 50 mm, cross-section at the center: trapezoidal, inner surface, lined with Teflon (registered trademark)), in an air-open system. Meanwhile, the vat-type container was heated until the surface temperature reached 100° C., by using a hot plate (manufactured by As One Corp.; NEO HOTPLATE HI-1000).

As soon as the aqueous monomer solution was poured into the vat-type container, a polymerization reaction was initiated. The polymerization reaction proceeded such that the product expanded and foamed vertically and laterally while steam was generated. Thereafter, the reaction product shrunk to a size slightly larger than the size of the vat-type container. This expansion and shrinkage was completed within about one minute. After 4 minutes from the initiation of the polymerization reaction, a hydrous gel-like polymer (hydrous gel) was taken out.

The hydrous gel obtained by the polymerization reaction was crushed by using a meat chopper (ROYAL MEATCHOPPER VR400K; manufactured by Iizuka Electric Industry Co., Ltd.; dies diameter: 9.5 mm), and thus a finely granulated water-containing gel-like cross-linked polymer was obtained.

The finely granulated water-containing gel-like crosslinked polymer was spread on a wire screen having a mesh size of 300 μm (50-mesh), and the water-containing gel-like cross-linked polymer was hot air dried for 50 minutes at 180° C. Subsequently, the polymer was pulverized with a roll mill, and was further classified with JIS standard sieves having mesh sizes of 850 μm and 150 μm. Through this series of operations, water-absorbing resin particles (8) of an irregular pulverized shape, having a mass median particle size (D50) of 450 μm and a logarithmic standard deviation (σζ) of the particle size distribution of 0.42, were obtained. The centrifuge retention capacity (CRC) of the water-absorbing resin particles (8) thus obtained was 36 [g/g], and the water-extractable (Ext) was 12% by weight.

Production Example 9

Production was carried out according to, among the water-absorbing agents described in Examples of Patent Literature 2, Example 1 that exhibited the highest centrifuge retention capacity and the highest absorption against pressure.

That is, 4.0 g of polyethylene glycol diacrylate (average number of added moles of ethylene oxide 8) was dissolved in 5500 g (monomer concentration: 38% by weight) of an aqueous solution of sodium acrylate having a neutralization ratio of 75% by mole, and this was used as a reaction liquid. Subsequently, this reaction liquid was degassed for 30 minutes in a nitrogen gas atmosphere.

Subsequently, in a reactor formed by attaching a lid to a double-blade type jacketed stainless steel kneader having two sigma-shaped blades and having an internal capacity of 10 L, the reaction liquid was supplied, and while the reaction liquid was maintained at 30° C., the system was purged with nitrogen gas.

Subsequently, while the reaction liquid was stirred, 2.8 g of sodium persulfate and 0.01 g of L-ascorbic acid were separately added thereto. After about one minute, polymerization was initiated. Furthermore, polymerization was carried out at 30° C. to 90° C. while the water-containing gel-like crosslinked polymer thus produced was crushed. After 60 minutes from the initiation of polymerization, the water-containing gel-like crosslinked polymer was taken out from the reactor. Meanwhile, the water-containing gel-like crosslinked polymer thus obtained was finely granulated to particles having a diameter of about 5 mm.

The finely granulated water-containing gel-like crosslinked polymer was spread on a wire screen having a mesh size of 300 μm (50-mesh) and was hot air dried for 90 minutes at 150° C. Subsequently, the water-containing gel-like crosslinked polymer was pulverized with a vibratory mill, further classified with a JIS standard sieve having a mesh size of 850 μm, and prepared. Through this series of operations, water-absorbing resin particles (9) of an irregular pulverized shape, having a mass median particle size (D50) of 380 μm and a logarithmic standard deviation (σζ) of the particle size distribution of 0.40, were obtained. The centrifuge retention capacity (CRC) of the water-absorbing resin particles (9) thus obtained was 38 [g/g], and the water-extractable (Ext) was 14% by weight.

TABLE 1

| | | D50 [μm] | σζ | CRC [g/g] | CRC after solids content compensation [g/g] | Ext [wt %] | Moisture content ratio (180° C./3 hr) |
|---|---|---|---|---|---|---|---|
| Production Example 1 | Water-absorbing resin particles (1) | 458 | 0.40 | 42 | 43 | 13 | 3.2 |
| Production Example 2 | Water-absorbing resin particles (2) | 380 | 0.35 | 39 | 40 | 11 | 3.0 |
| Production Example 3 | Water-absorbing resin particles (3) | 380 | 0.33 | 45 | 47 | 15 | 3.3 |
| Production Example 4 | Water-absorbing resin particles (4) | 470 | 0.42 | 36 | 37 | 9 | 3.3 |
| Production Example 5 | Water-absorbing resin particles (5) | 470 | 0.42 | 55 | 57 | 20 | 3.1 |

TABLE 1-continued

|  |  | D50 [μm] | σζ | CRC [g/g] | CRC after solids content compensation [g/g] | Ext [wt %] | Moisture content ratio (180° C./3 hr) |
|---|---|---|---|---|---|---|---|
| Production Example 6 | Water-absorbing resin particles (6) | 470 | 0.42 | 53 | 55 | 17 | 3.4 |
| Production Example 7 | Water-absorbing resin particles (7) | 455 | 0.41 | 33 | 34 | 8 | 3.3 |
| Production Example 8 | Water-absorbing resin particles (8) | 450 | 0.42 | 36 | 37 | 12 | 3.5 |
| Production Example 9 | Water-absorbing resin particles (9) | 380 | 0.40 | 38 | 39 | 14 | 3.4 |

Example 1

As a surface-crosslinking treatment, 100 parts by weight of the water-absorbing resin particles (1) obtained in Production Example 1 were uniformly mixed with an aqueous solution of surface crosslinking agent containing 0.5 parts by weight of propylene glycol, 0.3 parts by weight of 1,4-butanediol and 1.0 part by weight of pure water, and the mixture was subjected to a heating treatment at 210° C. for 40 minutes. Thus, a surface-crosslinked water-absorbing resin (hereinafter, indicated as "water-absorbing resin powder") (1) was obtained. Meanwhile, the heating treatment was carried out by stirring the mixture in a stainless steel container immersed in an oil bath. The general performance of the water-absorbing resin powder (1) thus obtained is presented in Table 2.

Subsequently, as a polycation addition treatment, a liquid mixture containing 0.9 parts by weight of a 27.5% by weight (8% by weight in terms of aluminum oxide) of aqueous solution of aluminum sulfate, 0.13 parts by weight of a 60% by weight of aqueous solution of sodium lactate and 0.025 parts by weight of propylene glycol was added to 100 parts by weight of the water-absorbing resin powder (1), and then the mixture was dried without air flow, at 60° C. for one hour. Thereafter, the resin powder was crushed until the particles could pass through a JIS standard sieve having a mesh size of 850 μm, and thus a particulate water-absorbing agent (1) was obtained. The general performance of the particulate water-absorbing agent (1) thus obtained is presented in Table 3.

Furthermore, a mini absorber and a disposable diaper type absorber as described in the section (5-12) were produced by using the particulate water-absorbing agent (1) thus obtained, and the absolute absorption amount, the re-wet amount, and the liquid absorption time of each of the absorbent cores were measured. The evaluation results for the mini absorber are presented in Table 3, and the evaluation results for the disposable diaper type absorber are presented in Table 4.

Example 2

The same operation as that carried out in Example 1 was carried out, except that in connection with the surface-crosslinking treatment of Example 1, the water-absorbing resin particles (1) were changed to the water-absorbing resin particles (2), and the heating treatment time was changed to 35 minutes, respectively. Thus, a water-absorbing resin powder (2) was obtained. The general performance of the water-absorbing resin powder (2) thus obtained is presented in Table 2.

Subsequently, the same polycation addition treatment as that carried out in Example 1 was carried out, and thus a particulate water absorbing agent (2) was obtained. The general performance of the particulate water-absorbing agent (2) thus obtained is presented in Table 3.

Furthermore, a mini absorber and a disposable diaper type absorber as described in the section (5-12) were produced by using the particulate water-absorbing agent (2) thus obtained, and the absolute absorption amount, the re-wet amount, and the liquid absorption time of each of the absorbent cores were measured. The evaluation results for the mini absorber are presented in Table 3, and the evaluation results for the disposable diaper type absorber are presented in Table 4.

Example 3

The same operation as that carried out in Example 1 was carried out, except that in connection with the surface-crosslinking treatment of Example 1, the heating treatment time was changed to 35 minutes. Thus, a water-absorbing resin powder (3) was obtained. The general performance of the water-absorbing resin powder (3) thus obtained is presented in Table 2.

Subsequently, the same polycation addition treatment as that carried out in Example 1 was carried out, and thus a particulate water-absorbing agent (3) was obtained. The general performance of the particulate water-absorbing agent (3) thus obtained is presented in Table 3.

Furthermore, a mini absorber as described in the section (5-12) was produced by using the particulate water-absorbing agent (3) thus obtained, and the absolute absorption amount and the re-wet amount were measured. The evaluation results for the mini absorber are presented in Table 3.

Example 4

The same operation as that carried out in Example 1 was carried out, except that in connection with the surface-crosslinking treatment of Example 1, the water-absorbing resin particles (1) were changed to the water-absorbing resin particles (3), and the heating treatment time was changed to 35 minutes, respectively. Thus, a water-absorbing resin powder (4) was obtained. The general performance of the water-absorbing resin powder (4) thus obtained is presented in Table 2.

Subsequently, the same polycation addition treatment as that carried out in Example 1 was carried out, and thus a particulate water-absorbing agent (4) was obtained. The general performance of the particulate water-absorbing agent (4) thus obtained is presented in Table 3.

Furthermore, a mini absorber as described in the section (5-12) was produced by using the particulate water-absorbing agent (4) thus obtained, and the absolute absorption amount and the re-wet amount were measured. The evaluation results for the mini absorber are presented in Table 3.

Example 5

The same operation as that carried out in Example 1 was carried out, except that in connection with the surface-crosslinking treatment of Example 1, the heating treatment time was changed to 45 minutes. Thus, a water-absorbing resin powder (5) was obtained. The general performance of the water-absorbing resin powder (5) thus obtained is presented in Table 2.

Subsequently, the same polycation addition treatment as that carried out in Example 1 was carried out, and thus a particulate water-absorbing agent (5) was obtained. The general performance of the particulate water-absorbing agent (5) thus obtained is presented in Table 3.

Furthermore, a mini absorber and a disposable diaper type absorber as described in the section (5-12) were produced by using the particulate water-absorbing agent (5) thus obtained, and the absolute absorption amount, the re-wet amount, and the liquid absorption time of each of the absorbent cores were measured. The evaluation results for the mini absorber are presented in Table 3, and the evaluation results for the disposable diaper type absorber are presented in Table 4.

Example 6

The same operation as that carried out in Example 1 was carried out, except that in connection with the surface-crosslinking treatment of Example 1, the water-absorbing resin particles (1) were changed to the water-absorbing resin particles (6), and the heating treatment conditions were changed to 215° C. and 50 minutes, respectively. Thus, a water-absorbing resin powder (6) was obtained. The general performance of the water-absorbing resin powder (6) thus obtained is presented in Table 2.

Subsequently, the same polycation addition treatment as that carried out in Example 1 was carried out, and thus a particulate water-absorbing agent (6) was obtained. The general performance of the particulate water-absorbing agent (6) thus obtained is presented in Table 3.

Furthermore, a mini absorber as described in the section (5-12) was produced by using the particulate water-absorbing agent (6) thus obtained, and the absolute absorption amount and the re-wet amount were measured. The evaluation results for the mini absorber are presented in Table 3.

Example 7

The same operation as that carried out in Example 1 was carried out, except that in connection with the polycation addition treatment of Example 1, the liquid mixture was changed to 1.0 part by weight (solids content of polycation: corresponding to 0.1% by weight) of a 10% by weight of aqueous solution of polyallylamine (trade name: PAA-10C, manufactured by Nitto Boseki Co., Ltd., molecular weight: about 10,000, cation density: 17.5 mmol/g). Thus, a particulate water-absorbing agent (7) was obtained. The general performance of the particulate water-absorbing agent (7) thus obtained is presented in Table 3.

Furthermore, a mini absorber as described in the section (5-12) was produced by using the particulate water-absorbing agent (7) thus obtained, and the absolute absorption amount and the re-wet amount were measured. The evaluation results for the mini absorber are presented in Table 3.

Example 8

The same operation as that carried out in Example 7 was carried out, except that the amount of addition of the aqueous solution of polyallylamine used in Example 7 was changed to 2.0 parts by weight, and thus a particulate water-absorbing agent (8) was obtained. The general performance of the particulate water-absorbing agent (8) thus obtained is presented in Table 3.

Furthermore, a mini absorber as described in the section (5-12) was produced by using the particulate water-absorbing agent (8) thus obtained, and the absolute absorption amount and the re-wet amount were measured. The evaluation results for the mini absorber are presented in Table 3.

Example 9

The same operation as that carried out in Example 7 was carried out, except that 1.0 part by weight of the aqueous solution of polyallylamine used in Example 7 was changed to 0.4 parts by weight (solids content of polycation: corresponding to 0.1% by weight) of a mixed solution containing 2.0 parts by weight of Unisence KHE102L (dimethylamine/ammonia/epichlorohydrin resin; an aqueous solution having an average molecular weight of about 70,000 (reference value), a pH of 1% by weight of aqueous solution of about 6, and a solids concentration of 50% by weight; manufactured by Senka Corp., cation density: 5.3 mmol/g) and 2.0 parts by weight of methanol, and thus a particulate water-absorbing agent (9) was obtained. The general performance of the particulate water-absorbing agent (9) thus obtained is presented in Table 3.

Furthermore, a mini absorber as described in the section (5-12) was produced by using the particulate water-absorbing agent (9) thus obtained, and the absolute absorption amount and the re-wet amount were measured. The evaluation results for the mini absorber are presented in Table 3.

Example 10

The same operation as that carried out in Example 9 was carried out, except that the amount of addition of the mixed solution containing Unisence KHE102L and methanol was changed to 0.8 parts by weight (solids content of polycation: corresponding to 0.2% by weight), and thus a particulate water-absorbing agent (10) was obtained. The general performance of the particulate water-absorbing agent (10) thus obtained is presented in Table 3.

Furthermore, a mini absorber as described in the section (5-12) was produced by using the particulate water-absorbing agent (10) thus obtained, and the absolute absorption amount and the re-wet amount were measured. The evaluation results for the mini absorber are presented in Table 3.

Example 11

The same operation as that carried out in Example 1 was carried out, except that 0.10 parts by weight of water-insoluble fine particles (Aerosil (registered trademark) 200; manufactured by Nippon Aerosil Co., Ltd.) were added and mixed, instead of the polycation addition treatment of Example 1. Thus, a particulate water-absorbing agent (11)

was obtained. The general performance of the particulate water-absorbing agent (11) thus obtained is presented in Table 3.

Furthermore, a mini absorber as described in the section (5-12) was produced by using the particulate water-absorbing agent (11) thus obtained, and the absolute absorption amount and the re-wet amount were measured. The evaluation results for the mini absorber are presented in Table 3.

Example 12

The same operation as that carried out in Example 1 was carried out, except that in addition to the polycation addition treatment of Example 1, 0.01 parts by weight of trisodium diethylenetriamine pentaacetate and 0.5 parts by weight of a leaf extract solution of a plant of the Theaceae family (trade name: FS-80MO, distributor: Shiraimatsu Pharmaceutical Co., Ltd.) were added and mixed. Thus, a particulate water-absorbing agent (12) was obtained. The general performance of the particulate water-absorbing agent (12) thus obtained is presented in Table 3.

Comparative Example 1

The same operation as that carried out in Example 1 was carried out, except that in connection with the surface crosslinking treatment of Example 1, the water-absorbing resin particles (1) were changed to the water-absorbing resin particles (4), and the heating treatment time was changed to 35 minutes, respectively. Thus, a comparative water-absorbing resin powder (1) was obtained. The general performance of the comparative water-absorbing resin powder (1) thus obtained is presented in Table 2.

Subsequently, the same polycation addition treatment as that carried out in Example 1 was carried out, and thus a comparative particulate water-absorbing agent (1) was obtained. The general performance of the comparative particulate water-absorbing agent (1) thus obtained is presented in Table 3.

Furthermore, a mini absorber and a disposable diaper type absorber as described in the section (5-12) were produced by using the comparative particulate water-absorbing agent (1) thus obtained, and the absolute absorption amount, the re-wet amount, and the liquid absorption time of each of the absorbent cores were measured. The evaluation results for the mini absorber are presented in Table 3, and the evaluation results for the disposable diaper type absorber are presented in Table 4.

Comparative Example 2

The same operation as that carried out in Example 1 was carried out, except that in connection with the surface cross-linking treatment of Example 1, the water-absorbing resin particles (1) were changed to the water-absorbing resin particles (5), and the heating treatment time was changed to 50 minutes, respectively. Thus, a comparative water-absorbing resin powder (2) was obtained. The general performance of the comparative water-absorbing resin powder (2) thus obtained is presented in Table 2.

Subsequently, the same polycation addition treatment as that carried out in Example 1 was carried out, and thus a comparative particulate water-absorbing agent (2) was obtained. The general performance of the comparative particulate water-absorbing agent (2) thus obtained is presented in Table 3.

Furthermore, a mini absorber as described in the section (5-12) was produced by using the comparative particulate water-absorbing agent (2) thus obtained, and the absolute absorption amount and the re-wet amount were measured. The evaluation results for the mini absorber are presented in Table 3.

Comparative Example 3

As a surface crosslinking treatment, an aqueous solution of surface crosslinking agent containing 0.4 parts by weight of 1,4-butanediol, 0.6 parts by weight of propylene glycol, and 3.0 parts by weight of pure water was uniformly mixed with 100 parts by weight of the water-absorbing resin particles (8) obtained in Production Example 8, and the mixture was heat treated for 30 minutes at 200° C. Meanwhile, the heating treatment was carried out by stirring the mixture in a stainless steel container immersed in an oil bath. Thereafter, the resin particles were crushed until the particles could pass through a JIS standard sieve having a mesh size of 850 μm, and the particles were further subjected to Paint Shaker Test 1 (disclosed in JP 2005-344103 A). Thereby, a comparative water-absorbing resin powder (3) was obtained. The general performance of the comparative water-absorbing resin powder (3) thus obtained is presented in Table 2.

Subsequently, as a polycation addition treatment, a uniform liquid mixture containing 0.5 parts by weight of a 27% by weight of aqueous solution of aluminum sulfate as a liquid for tap water (manufactured by Asada Chemical Co., Ltd.), 0.1 parts by weight of a 50% by weight of aqueous solution of sodium lactate (manufactured by Musashino Chemical Laboratory, Ltd.) and 0.05 parts by weight of propylene glycol, relative to 100 parts by weight of the comparative water-absorbing resin powder (3), was prepared.

Subsequently, in a mixing apparatus (Lödige mixer) having the jacket temperature set to 70° C., 500 g of the comparative water-absorbing resin powder (3) that had been heated in advance to 70° C. was introduced, and 3.35 g of the liquid mixture was applied to the powder by a pressurized spray under the conditions of a speed of rotation of 250 rpm. The mixture was mixed for 30 seconds, and then the comparative water-absorbing resin powder (3) discharged from the mixing apparatus was left to stand for 3 minutes at room temperature. Subsequently, the particles were crushed until the particles could pass through a JIS standard sieve having a mesh size of 850 μm. Thereafter, the particles were further subjected to Paint Shaker Test 2 (disclosed in JP 2005-344103 A), and thereby a comparative particulate water-absorbing agent (3) was obtained. The general performance of the comparative particulate water-absorbing agent (3) thus obtained is presented in Table 3.

Furthermore, a mini absorber and a disposable diaper type absorber as described in the section (5-12) were produced by using the comparative particulate water-absorbing agent (3) thus obtained, and the absolute absorption amount, the re-wet amount, and the liquid absorption time of each of the absorbent cores were measured. The evaluation results for the mini absorber are presented in Table 3, and the evaluation results for the disposable diaper type absorber are presented in Table 4.

Comparative Example 4

The same operation as that carried out in Example 1 was carried out, except that 1 part by weight of pure water was added and mixed instead of the polycation addition treatment of Example 1, and thus a comparative particulate water-absorbing agent (4) was obtained. The general performance of the comparative particulate water-absorbing agent (4) thus obtained is presented in Table 3.

Furthermore, a mini absorber and a disposable diaper type absorber as described in the section (5-12) were produced by using the comparative particulate water-absorbing agent (4) thus obtained, and the absolute absorption amount, the re-wet amount, and the liquid absorption time of each of the absorbent cores were measured. The evaluation results for the mini absorber are presented in Table 3, and the evaluation results for the disposable diaper type absorber are presented in Table 4.

Comparative Example 5

As a surface crosslinking treatment, 100 parts by weight of the water-absorbing resin particles (7) obtained in Production Example 7 were uniformly mixed with an aqueous solution of surface crosslinking agent containing 0.5 parts by weight of propylene glycol, 0.3 parts by weight of 1,4-butanediol and 1.0 part by weight of pure water, and the mixture was subjected to a heating treatment for 40 minutes at 210° C. Thus, a comparative water-absorbing resin powder (5) was obtained. Meanwhile, the heating treatment was carried out by stirring the mixture in a stainless steel container immersed in an oil bath. The general performance of the comparative water-absorbing resin powder (5) thus obtained is presented in Table 2.

Subsequently, as a polycation addition treatment, a liquid mixture containing 0.9 parts by weight of a 27.5% by weight (8% by weight in terms of aluminum oxide) of aqueous solution of aluminum sulfate, 0.13 parts by weight of a 60% by weight of aqueous solution of sodium lactate, and 0.025 parts by weight of propylene glycol, was added to 100 parts by weight of the comparative water-absorbing resin powder (5), and then the mixture was dried without air flow at 60° C. for one hour. Thereafter, the particles were crushed until the particles could pass through a JIS standard sieve having a mesh size of 850 μm. Thereafter, as a water-insoluble fine particle addition treatment, 0.50 parts by weight of Aerosil (registered trademark) 200 (manufactured by Nippon Aerosil Co., Ltd.) was added to and mixed with the powder, and thus a comparative particulate water-absorbing agent (5) was obtained. The general performance of the comparative particulate water-absorbing agent (5) thus obtained is presented in Table 3.

Furthermore, a mini absorber and a disposable diaper type absorber as described in the section (5-12) were produced by using the comparative particulate water-absorbing agent (5) thus obtained, and the absolute absorption amount, the re-wet amount, and the liquid absorption time of each of the absorbent cores were measured. The evaluation results for the mini absorber are presented in Table 3, and the evaluation results for the disposable diaper type absorber are presented in Table 4.

Comparative Example 6

Thereafter, as a water-insoluble fine particle addition treatment, 0.50 parts by weight of Aerosil (registered trademark) 200 (manufactured by Nippon Aerosil Co., Ltd.) was added to and mixed with 100 parts by weight of the comparative particulate water-absorbing agent (1) obtained in Comparative Example 1, and thus a comparative particulate water-absorbing agent (6) was obtained. The general performance of the comparative particulate water-absorbing agent (6) thus obtained is presented in Table 3.

Furthermore, a mini absorber as described in the section (5-12) was produced by using the comparative particulate water-absorbing agent (6) thus obtained, and the absolute absorption amount and the re-wet amount were measured. The evaluation results for the mini absorber are presented in Table 3.

Comparative Example 7

As a surface crosslinking treatment, 100 parts by weight of the water-absorbing resin particles (9) obtained in Production Example 9 were uniformly mixed with an aqueous solution of surface crosslinking agent consisting of 0.5 parts by weight of propylene glycol, 0.03 parts by weight of ethylene glycol diglycidyl ether, 0.3 parts by weight of 1,4-butanediol, and 3.0 parts by weight of pure water, and the mixture was subjected to a heating treatment at 200° C. for 55 minutes. Thus, a comparative water-absorbing resin powder (7) was obtained. Meanwhile, the heating treatment was carried out by stirring the mixture in a stainless steel container immersed in an oil bath. The general performance of the comparative water-absorbing resin powder (7) thus obtained is presented in Table 2.

Subsequently, as a polycation addition treatment, 5.4 parts by weight of a 51.2% by weight of aqueous solution of aluminum sulfate tetradecahydrate to octadecahydrate was added to 100 parts by weight of the comparative water-absorbing resin powder (7), and the mixture was dried without air flow at 60° C. for one hour. Thereafter, the particles were crushed until the particles could pass through a JIS standard sieve having a mesh size of 850 μm, and thus a comparative particulate water-absorbing agent (7) was obtained. The general performance of the comparative particulate water-absorbing agent (7) thus obtained is presented in Table 3.

Furthermore, a mini absorber as described in the section (5-12) was produced by using the comparative particulate water-absorbing agent (7) thus obtained, and the absolute absorption amount and the re-wet amount were measured. The evaluation results for the mini absorber are presented in Table 3.

Comparative Example 8

The same operation as that carried out in Example 7 was carried out, except that the amount of addition of the aqueous solution of polyallylamine used in Example 7 was changed to 3.0 parts by weight, and thus a comparative particulate water-absorbing agent (8) was obtained. The general performance of the comparative particulate water-absorbing agent (8) thus obtained is presented in Table 3.

Furthermore, a mini absorber as described in the section (5-12) was produced by using the comparative particulate water-absorbing agent (8) thus obtained, and the absolute absorption amount and the re-wet amount were measured. The evaluation results for the mini absorber are presented in Table 3.

Comparative Example 9

The same operation as that carried out in Example 9 was carried out, except that in connection with the polycation addition treatment in Example 9, the amount of addition of the mixed solution containing Unisence KHE102L and methanol was changed to 4.0 parts by weight, and thus a comparative particle water-absorbing agent (9) was obtained. The general performance of the comparative particulate water-absorbing agent (9) thus obtained is presented in Table 3.

Furthermore, a mini absorber as described in the section (5-12) was produced by using the comparative particulate water-absorbing agent (9) thus obtained, and the absolute absorption amount and the re-wet amount were measured. The evaluation results for the mini absorber are presented in Table 3.

Comparative Example 10

The same operation as that carried out in Example 11 was carried out, except that the amount of addition of the water-insoluble fine particles (Aerosil (registered trademark) 200; manufactured by Nippon Aerosil Co., Ltd.) used in Example 11 was changed to 1.0 part by weight, and thus a comparative particulate water-absorbing agent (10) was obtained. The general performance of the comparative particulate water-absorbing agent (10) thus obtained is presented in Table 3.

Furthermore, a mini absorber as described in the section (5-12) was produced by using the comparative particulate water-absorbing agent (10) thus obtained, and the absolute absorption amount and the re-wet amount were measured. The evaluation results for the mini absorber are presented in Table 3.

TABLE 2

| | | Centrifuge retention capacity (CRC) | Centrifuge retention capacity (CRC) after solids content compensation | Absorption against pressure (AAP) | Absorption against pressure (AAP) after solids content compensation | Moisture content ratio (180° C./3 hr) | ΔCRC[1] |
|---|---|---|---|---|---|---|---|
| Example 1 | Water-absorbing resin powder (1) | 33 | 34 | 26 | 26 | 1.5 | 9 |
| Example 2 | Water-absorbing resin powder (2) | 32 | 32 | 25 | 25 | 1.4 | 7 |
| Example 3 | Water-absorbing resin powder (3) | 35 | 353 | 27 | 27 | 1.3 | 7 |
| Example 4 | Water-absorbing resin powder (4) | 36 | 36 | 24 | 24 | 1.0 | 9 |
| Example 5 | Water-absorbing resin powder (5) | 32 | 32 | 25 | 25 | 1.1 | 10 |
| Example 6 | Water-absorbing resin powder (6) | 37 | 38 | 21 | 21 | 1.4 | 15 |
| Comparative Example 1 | Comparative water-absorbing resin powder (1) | 33 | 33 | 24 | 24 | 1.3 | 3 |
| Comparative Example 2 | Comparative water-absorbing resin powder (2) | 34 | 34 | 20 | 20 | 1.2 | 21 |
| Comparative Example 3 | Comparative water-absorbing resin powder (3) | 31 | 31 | 25 | 25 | 1.1 | 5 |
| Comparative Example 5 | Comparative water-absorbing resin powder (5) | 26 | 26 | 23 | 23 | 1.3 | 7 |
| Comparative Example 7 | Comparative water-absorbing resin powder (7) | 33 | 33 | 23 | 23 | 1.2 | 5 |

[1] Centrifuge retention capacity (CRC) of the water-absorbing resin obtainable before surface crosslinking-centrifuge retention capacity (CRC) of the water-absorbing resin obtainable after surface crosslinking

TABLE 3

| | Performance of particulate water-absorbing agent | | | | | | Performance of mini absorber | |
|---|---|---|---|---|---|---|---|---|
| | Centrifuge retention capacity (CRC) [g/g] | Free swell capacity (FSC) [g/g] | Absorption against pressure (AAP-4.83 kPa) [g/g] | Vertical diffusion absorption amount under pressure (VDAUP) [g] | hysiological saline flow conductivity (SFC) [(1)] | Moisture content ratio (105° C./3 h) [wt %] | Absolute absorption amount [g] | Re-wet amount [g] |
| Example 1 | 33 | 57 | 25 | 62 | 21 | 0.7 | 310 | 1.0 |
| Example 2 | 32 | 58 | 24 | 47 | 25 | 0.7 | 320 | 0.5 |
| Example 3 | 35 | 60 | 27 | 41 | 10 | 0.7 | 340 | 1.0 |
| Example 4 | 36 | 63 | 23 | 35 | 3 | 0.7 | 0350 | 1.0 |
| Example 5 | 32 | 57 | 25 | 59 | 24 | 0.7 | 310 | 0.5 |
| Example 6 | 37 | 64 | 20 | 35 | 1 | 0.7 | 360 | 2.0 |
| Example 7 | 33 | 57 | 22 | 42 | 15 | 1.0 | 315 | 1.0 |
| Example 8 | 33 | 61 | 21 | 35 | 14 | 1.2 | 335 | 1.0 |

TABLE 3-continued

Performance of particulate water-absorbing agent

| | Centrifuge retention capacity (CRC) [g/g] | Free swell capacity (FSC) [g/g] | Absorption against pressure (AAP-4.83 kPa) [g/g] | Vertical diffusion absorption amount under pressure (VDAUP) [g] | hysiological saline flow conductivity (SFC) [(1)] | Performance of mini absorber | | |
|---|---|---|---|---|---|---|---|---|
| | | | | | | Moisture content ratio (105° C./ 3 h) [wt %] | Absolute absorption amount [g] | Re-wet amount [g] |
| Example 9 | 33 | 59 | 22 | 40 | 18 | 1.0 | 325 | 1.0 |
| Example 10 | 33 | 61 | 21 | 35 | 17 | 1.2 | 330 | 1.0 |
| Example 11 | 33 | 57 | 23 | 48 | 17 | 1.0 | 310 | 1.0 |
| Example 12 | 33 | 57 | 25 | 61 | 20 | 0.9 | 310 | 1.0 |
| Comparative Example 1 | 33 | 52 | 23 | 29 | 15 | 0.7 | 280 | 6.0 |
| Comparative Example 2 | 34 | 56 | 20 | 23 | 13 | 0.7 | 310 | 4.0 |
| Comparative Example 3 | 31 | 51 | 25 | 59 | 45 | 0.7 | 270 | 1.0 |
| Comparative Example 4 | 33 | 48 | 24 | 50 | 21 | 1.5 | 250 | 2.0 |
| Comparative Example 5 | 26 | 55 | 19 | 64 | 80 | 0.7 | 300 | 7.0 |
| Comparative Example 6 | 33 | 58 | 18 | 25 | 13 | 0.7 | 340 | 6.0 |
| Comparative Example 7 | 33 | 56 | 21 | 29 | 15 | 0.7 | 310 | 4.0 |
| Comparative Example 8 | 33 | 63 | 21 | 26 | 15 | 1.2 | 330 | 4.0 |
| Comparative Example 9 | 33 | 66 | 20 | 28 | 11 | 1.5 | 340 | 5.0 |
| Comparative Example 10 | 33 | 59 | 18 | 29 | 10 | 1.0 | 310 | 4.0 |

(1): $[\times 10^{-7} \cdot cm^3 \cdot s \cdot g^{-1}]$ (Inference 1)

From Table 3, it is understood that in a comparison of Examples 1 to 6 and Comparative Examples 1 to 7, a particulate water-absorbing agent which satisfies an free swell capacity (FSC) of 55 [g/g] or greater, a vertical diffusion absorption amount under pressure (VDAUP) of 30 g or greater, and an absorption against pressure (AAP—4.83 kPa) of 20 [g/g] or greater, exhibits an absolute absorption amount (mini absorber) as defined in the section (5-12) (2-a) of 300 g or greater, and a re-wet amount (mini absorber) as defined in the section (5-12) (2-b) of 2 g or less. That is, the absolute absorption amount and the re-wet amount that are conventionally contradictory to each other can be balanced to a large extent, and thus a satisfactory absorber can be provided.

From Table 1 to Table 3, it is understood that in a comparison of Examples 1, 2 and 6 and Comparative Examples 1 to 3 and 7, when water-absorbing resin particles having an centrifuge retention capacity (CRC) of 40 to 56 [g/g] are surface-crosslinked, a particulate water-absorbing agent which is satisfactorily balanced between the free swell capacity (FSC), the vertical diffusion absorption amount under pressure (VDAUP), and the absorption against pressure (AAP—4.83 kPa) may be provided.

From Table 2, it is found that in a comparison between Examples 1, 3 and 5 and Comparative Examples 4 and 5, when a polyvalent metal cation is incorporated into a surface-crosslinked water-absorbing resin a particulate water-absorbing agent which is satisfactorily balanced between the free swell capacity (FSC), the vertical diffusion absorption amount under pressure (VDAUP), and the absorption against pressure (AAP—4.83 kPa) may be provided.

Furthermore, Comparative Example 6 is a resultant obtained by adding and mixing 0.5 parts by weight of a silicon dioxide fine powder as water-insoluble fine particles, to the comparative particulate water absorbent 1 obtained in Comparative Example 1. As indicated in Table 3, the free swell capacity (FSC) slightly increases (52 [g/g]→58 [g/g]) as compared with Comparative Example 1, but the water absorption performance under pressure decreases significantly (AAP; 23 [g/g]→>18 [g/g], VDAUP: 29 [g/g]→25 [g/g]). As a result, the re-wet amount is 6 g, which is much larger than the re-wet amount of mini absorbers (0.5 to 2 g) in Examples of the present invention, and Comparative Example 6 is inferior in the performance as an absorbent core. Furthermore, even in a comparison with Example 11 (addition of 0.1 parts by weight of a silicon dioxide fine powder), it is understood that when water-insoluble inorganic fine particles are used as a spacer, the using amount of the spacer is also important.

Furthermore, Comparative Example 3 is an Example which has the highest centrifuge retention capacity (CRC) and the highest absorption against pressure (AAP) and is well-balanced in Patent Literature 1 (JP 2005-344103 A). However, the absolute absorption amount of the mini absorber (Table 3) is 270 g, so that the absolute absorption amount of Comparative Example 3 is much inferior as compared with the absolute absorption amounts of Examples 1 to 6 of the present invention (310 g to 360 g).

Furthermore, Comparative Example 7 is an Example which has the highest centrifuge retention capacity (CRC) and the highest absorption against pressure (AAP) and is well-balanced in Patent Literature 2 (JP 2005-113117 A). However, the re-wet amount of the mini absorber (Table 3) is 4 g, so that the re-wet amount of Comparative Example 7 is much inferior as compared with the re-wet amounts of Examples 1 to 6 of the present invention (0.5 g to 2 g).

TABLE 4

Evaluation of liquid absorption time, re-wet amount (re-wet), and absolute absorption amount of paper diaper type absorbers

| | Core concentration; 30 wt % | | | Core concentration; 40 wt % | | | Core concentration; 50 wt % | | |
|---|---|---|---|---|---|---|---|---|---|
| | Liquid absorption time [sec] | Re-wet amount [g] | Absolute absorption amount [g] | Liquid absorption time [sec] | Re-wet amount [g] | Absolute absorption amount [g] | Liquid absorption time [sec] | Re-wet amount [g] | Absolute absorption amount [g] |
| Example 1 | 125 | 33 | 824 | 118 | 21 | 777 | 240 | 15 | 754 |
| Example 2 | 130 | 32 | 836 | 110 | 20 | 786 | 220 | 15 | 756 |
| Example 5 | 125 | 35 | 822 | 115 | 22 | 774 | 230 | 14 | 744 |
| Comparative Example 1 | 130 | 35 | 760 | 150 | 30 | 714 | 360 | 21 | 680 |
| Comparative Example 3 | 140 | 35 | 748 | 130 | 35 | 702 | 210 | 22 | 671 |
| Comparative Example 4 | 140 | 70 | 706 | 130 | 51 | 666 | 340 | 40 | 636 |
| Comparative Example 5 | 130 | 32 | 780 | 120 | 30 | 735 | 300 | 25 | 709 |

| | Core concentration; 60 wt % | | | Core concentration; 70 wt % | | |
|---|---|---|---|---|---|---|
| | Liquid absorption time [sec] | Re-wet amount [g] | Absolute absorption amount [g] | Liquid absorption time [sec] | Re-wet amount [g] | Absolute absorption amount [g] |
| Example 1 | 275 | 12 | 724 | 510 | 11 | 710 |
| Example 2 | 294 | 12 | 736 | 522 | 12 | 722 |
| Example 5 | 260 | 11 | 724 | 480 | 12 | 709 |
| Comparative Example 1 | 505 | 16 | 664 | 760 | 18 | 649 |
| Comparative Example 3 | 290 | 17 | 652 | 745 | 19 | 637 |
| Comparative Example 4 | 500 | 30 | 616 | 1000 | 40 | 601 |
| Comparative Example 5 | 510 | 19 | 690 | 780 | 20 | 675 |

(Inference 2)

Table 4 shows the evaluation results in the sections (5-12) (2-c) and (2-d) in relation to the various absorbing articles (pseudo-paper diapers for children) each containing 12 g of a particulate water-absorbing agent.

In a comparison of Examples 1, 2 and 5 and Comparative Examples 1, 3, 4 and 5, it is understood that when a particulate water-absorbing agent which satisfies an free swell capacity (FSC) of 55 [g/g] or greater, a vertical diffusion absorption amount under pressure (VDAUP) of 30 g or greater, and an absorption capacity under pressure (AAP—4.83 kPa) of 20 [g/g] or greater, is produced into a disposable diaper type absorber having a core concentration of 40% by weight or greater, and particularly 50% to 70% by weight, an absorbent core which is excellent in the liquid absorption time and the re-wet amount (re-wet) is obtained. That is, as compared with conventional particulate water-absorbing agents, the particulate water-absorbing agent of the present invention can be made to be well-balanced between the liquid absorption time, the re-wet amount and the absolute absorption amount, particularly when produced into an absorbing article having a core concentration of 40% by weight or greater. More specifically, an absorbing article having a core concentration of 40% by weight has "a liquid absorption time of 120 seconds or less, a re-wet amount of 25 g or less, and an absolute absorption amount of 750 g or more"; an absorbing article having a core concentration of 50% by weight has "a liquid absorption time of 240 seconds or less, a re-wet amount of 20 g or less, and an absolute absorption amount of 730 g or more"; an absorbing article having a core concentration of 60% by weight has "a liquid absorption time of 300 seconds or less, a re-wet amount of 13 g or less, and an absolute absorption amount of 710 g or more"; and an absorbing article having a core concentration of 70% by weight has "a liquid absorption time of 600 seconds or less, a re-wet amount of 15 g or less, and an absolute absorption amount of 700 g or more". As such, as compared with the conventional particulate water-absorbing agents, absorbers and absorbing articles produced by using the particulate water-absorbing agent of the present invention are well-balanced between the liquid absorption time and the re-wet amount, and are superior in quality.

CONCLUSIONS

As discussed above, when a particulate water-absorbing agent having an free swell capacity (FSC) of 55 [g/g] or greater, an absorption against pressure (AAP—4.83 kPa) of 20 [g/g] or greater, and a vertical diffusion absorption amount under pressure (VDAUP) of 30 [g/g] or greater is used in an absorbent core or an absorbing article, an absorbent core or an absorbing article which is excellent in the liquid absorption time, the re-wet amount and the absolute absorption amount, particularly an absorbent core or an absorbing article having a core concentration of 40% to 100% by weight, can be provided for the first time.

Furthermore, according to Table 3, when a mini absorber is constructed by using the particulate water-absorbing agent of the present invention, a satisfactory absolute absorption amount of 300 g or greater and a satisfactory re-wet amount of 2 g or less are obtained. Furthermore, according to Table 4, the particulate water-absorbing agent of the present invention provides an excellent absorber or absorbing article having a core concentration of 40% by weight, "a liquid absorption time of 120 seconds or less, a re-wet amount of 25 g or less, an absolute absorption amount of 750 g or more", and the like, which physical properties are not found in conventional particulate water-absorbing agents.

INDUSTRIAL APPLICABILITY

The particulate water-absorbing agent related to the present invention is appropriate for hygienic materials such as paper diapers, sanitary napkins, and incontinence pads.

REFERENCE SIGNS LIST

100 PLASTIC SUPPORTING CYLINDER
101 STAINLESS STEEL 400-MESH WIRE SCREEN
102 WATER-ABSORBING AGENT (SWOLLEN GEL)
103 PISTON
104 LOAD (WEIGHT)
105 PETRI DISH
106 GLASS FILTER
107 FILTER PAPER
108 0.90 WT % AQUEOUS SOLUTION OF SODIUM CHLORIDE

The invention claimed is:

1. A particulate water-absorbing agent comprising a surface-crosslinked polyacrylic acid (salt)-type water-absorbing resin as a main component, and comprising at least one spacer selected from a polycation and water-insoluble fine particles,
the particulate water-absorbing agent having a free swell capacity (FSC) of 55 to 65 [g/g], an absorption against pressure (AAP—4.83 kPa) of 20 to 30 [g/g], and a vertical diffusion absorption amount under pressure (VDAUP—4.83 kPa) of 30 to 80 g.

2. The particulate water-absorbing agent according to claim 1, wherein the polycation is a polyamine polymer having a molecular weight of 1,000 or greater.

3. The particulate water-absorbing agent according to claim 2, wherein the content of the polyamine polymer is greater than or equal to 0.001 parts by weight and less than 0.3 parts by weight, relative to 100 parts by weight of the water-absorbing resin.

4. The particulate water-absorbing agent according to claim 1, wherein the polycation is a water-soluble polyvalent metal cation.

5. The particulate water-absorbing agent according to claim 4, wherein the content of the water-soluble polyvalent metal cation is 0.001 parts to 3 parts by weight relative to 100 parts by weight of the water-absorbing resin.

6. The particulate water-absorbing agent according to claim 1, wherein the water-insoluble fine particles are inorganic fine particles.

7. The particulate water-absorbing agent according to claim 1, wherein the content of the water-insoluble fine particles is 0.001 parts to 0.4 parts by weight relative to 100 parts by weight of the water-absorbing resin.

8. The particulate water-absorbing agent according to claim 1, further comprising a polyhydric alcohol.

9. The particulate water-absorbing agent according to claim 8, wherein the polyhydric alcohol is propanediol.

10. The particulate water-absorbing agent according to claim 8, wherein the content of the polyhydric alcohol is 0.01 parts to 3 parts by weight relative to 100 parts by weight of the water-absorbing resin.

11. The particulate water-absorbing agent according to claim 1, further comprising an α-hydroxycarboxylic acid.

12. The particulate water-absorbing agent according to claim 11, wherein the content of the α-hydroxycarboxylic acid is 0.01 parts to 3 parts by weight relative to 100 parts by weight of the water-absorbing resin.

13. The particulate water-absorbing agent according to claim 1, wherein the polyacrylic acid (salt)-type water-absorbing resin is surface-crosslinked with a surface crosslinking agent other than a polycation.

14. The particulate water-absorbing agent according to claim 1, further comprising a plant component.

15. The particulate water-absorbing agent according to claim 14, wherein the content of the plant component is greater than 0 parts and less than or equal to 10 parts by weight relative to 100 parts by weight of the water-absorbing resin.

16. A method for producing a particulate water-absorbing agent comprising a polyacrylic acid (salt)-type water-absorbing resin as a main component, the method comprising a polymerization step for polymerizing a water-soluble unsaturated monomer comprising acrylic acid (salt) as a main component, a drying step, and a surface-crosslinking step, the method comprising the following steps (A), (B) and (D):
Step (A): a step for obtaining water-absorbing resin particles having an centrifuge retention capacity (CRC) of 40 to 56 [g/g] before the surface-crosslinking step;
Step (B): a step for surface-crosslinking the water-absorbing resin particles obtained in the step (A), and thereby obtaining a water-absorbing resin powder having an centrifuge retention capacity (CRC) of 32 to 40 [g/g] and an absorption against pressure (AAP—4.83 kPa) of 20 to 30 [g/g]; and
Step (D): a step for mixing 100 parts by weight of the water-absorbing resin powder obtained in the step (B) with 0.001 parts to 3 parts by weight of a polyvalent metal cation as an aqueous solution.

17. A method for producing a particulate water-absorbing agent comprising a polyacrylic acid (salt)-type water-absorbing resin as a main component, the method comprising a polymerization step for polymerizing a water-soluble unsaturated monomer comprising acrylic acid (salt) as a main component, a drying step, and a surface-crosslinking step,
the method comprising the following steps (A), (B) and (E):
Step (A): a step for obtaining water-absorbing resin particles having an centrifuge retention capacity (CRC) of 40 to 56 [g/g] before the surface-crosslinking step;
Step (B): a step for surface-crosslinking the water-absorbing resin particles obtained in the step (A), and thereby obtaining a water-absorbing resin powder having an centrifuge retention capacity (CRC) of 32 to 40 [g/g] and an absorption against pressure (AAP—4.83 kPa) of 20 to 30 [g/g]; and
Step (E): a step for mixing 100 parts by weight of the water-absorbing resin powder obtained in the step (B) with a polyamine polymer in an amount of greater than or equal to 0.001 parts and less than 0.3 parts by weight as an aqueous solution or a powder.

18. A method for producing a particulate water-absorbing agent comprising a polyacrylic acid (salt)-type water-absorbing resin as a main component, the method comprising a polymerization step for polymerizing a water-soluble unsaturated monomer comprising acrylic acid (salt) as a main component, a drying step, and a surface-crosslinking step, the method comprising the following steps (A), (B) and (F):

Step (A): a step for obtaining water-absorbing resin particles having an centrifuge retention capacity (CRC) of 40 to 56 [g/g] before the surface-crosslinking step;

Step (B): a step for surface-crosslinking the water-absorbing resin particles obtained in the step (A), and thereby obtaining a water-absorbing resin powder having an centrifuge retention capacity (CRC) of 32 to 40 [g/g] and an absorption against pressure (AAP—4.83 kPa) of 20 to 30 [g/g]; and Step (F): a step for mixing 100 parts by weight of the water-absorbing resin powder obtained in the step (B) with 0.001 parts to 0.4 parts by weight of water-insoluble fine particles as a powder.

19. The method according to claim 16, wherein, in the step (B), the decrement of the absorption capacity defined by the following formula is 7 [g/g] or greater:

Decrement of absorption capacity [g/g]={Centrifuge retention capacity (CRC) before surface crosslinking}−{Centrifuge retention capacity (CRC) after surface crosslinking} [Mathematical Formula 1]

20. The method according to claim 19, wherein the decrement of the absorption capacity is 16 [g/g] or less.

21. The method according to claim 16, wherein, in the step (B) or in the steps after the step (B), the polycation selected from a polyvalent metal cation or a polyamine polymer is incorporated as an aqueous solution comprising a polyhydric alcohol or an α-hydroxycarboxylic acid.

22. An absorbent core comprising the particulate water-absorbing agent according to claim 1.

23. The absorbent core according to claim 22, wherein the absorbent core is molded to comprise the particulate water-absorbing agent and optionally a fibrous base material, and the content of the particulate water-absorbing agent is 40% to 90% by weight.

24. An absorbing article comprising the absorbent core according to claim 22.

25. The absorbent core of claim 22, wherein the particulate water absorbing agent is prepared by the method of claim 16.

* * * * *